(12) United States Patent
Goode et al.

(10) Patent No.: US 7,582,070 B2
(45) Date of Patent: Sep. 1, 2009

(54) MODULAR HEMOSTATIC VALVE

(75) Inventors: Louis B. Goode, Cranberry Township, PA (US); Chun Kee Lui, Monroeville, PA (US); Robert Booker, Vandergrift, PA (US); Benjamin T. Ewing, Cranberry, PA (US)

(73) Assignee: Cook Vascular Incorporated, Leechburg, PA (US)

( * ) Notice: Subject to any disclaimer, the term of this patent is extended or adjusted under 35 U.S.C. 154(b) by 719 days.

(21) Appl. No.: 11/100,811

(22) Filed: Apr. 7, 2005

(65) Prior Publication Data

US 2005/0228346 A1    Oct. 13, 2005

Related U.S. Application Data

(60) Provisional application No. 60/560,914, filed on Apr. 9, 2004, provisional application No. 60/573,659, filed on May 21, 2004.

(51) Int. Cl.
*A61M 5/178* (2006.01)
(52) U.S. Cl. .................... 604/167.04; 604/160
(58) Field of Classification Search ................
604/167.01–167.06, 164.01, 164.04, 164.05; 606/167–189; 251/148
See application file for complete search history.

(56) References Cited

U.S. PATENT DOCUMENTS

| | | | |
|---|---|---|---|
| 4,626,245 A | 12/1986 | Weinstein | |
| 4,798,594 A | 1/1989 | Hillstead | |
| 4,886,507 A | 12/1989 | Patton et al. | |
| 4,895,346 A | 1/1990 | Steigerwald | |
| 4,895,565 A | 1/1990 | Hillstead | |
| 4,932,633 A | 6/1990 | Johnson et al. | |
| 5,006,113 A | 4/1991 | Fischer | |
| 5,125,903 A | 6/1992 | McLaughlin et al. | |
| 5,125,904 A | 6/1992 | Lee | |
| 5,149,327 A | 9/1992 | Oshiyama | |
| 5,167,636 A | 12/1992 | Clement | |
| 5,167,637 A | 12/1992 | Okada et al. | |
| 5,176,652 A | 1/1993 | Littrell | |
| 5,180,373 A | 1/1993 | Green et al. | |
| 5,207,656 A | 5/1993 | Kranys | |
| 5,267,966 A | 12/1993 | Paul | |
| 5,269,763 A | 12/1993 | Boehmer et al. | |
| 5,273,546 A | 12/1993 | McLaughlin et al. | |
| 5,282,790 A | 2/1994 | Clement | |
| 5,300,034 A | 4/1994 | Behnke et al. | |
| 5,300,046 A | 4/1994 | Scarfone et al. | |
| 5,304,143 A | 4/1994 | Green et al. | |
| 5,350,363 A | 9/1994 | Goode et al. | |
| 5,360,417 A | 11/1994 | Gravener et al. | |
| 5,389,081 A | 2/1995 | Castro | |
| 5,391,154 A | 2/1995 | Young | |

(Continued)

FOREIGN PATENT DOCUMENTS

WO    WO 2004/022125 A2    3/2004

*Primary Examiner*—Nicholas D Lucchesi
*Assistant Examiner*—Nathan R Price
(74) *Attorney, Agent, or Firm*—Brinks Hofer Gilson & Lione

(57) ABSTRACT

A modular hemostatic valve includes a splittable valve body. The splittable body defines a passageway. A sealing element positions in the passageway. The sealing element is configured to facilitate the passage of a first medical device, and the splittable valve body is configured to engage a second medical device.

15 Claims, 21 Drawing Sheets

U.S. PATENT DOCUMENTS

| | | |
|---|---|---|
| 5,453,095 A | 9/1995 | Davila et al. |
| 5,538,505 A | 7/1996 | Weinstein et al. |
| 5,562,632 A | 10/1996 | Davila et al. |
| 5,643,227 A | 7/1997 | Stevens |
| 5,685,854 A | 11/1997 | Green et al. |
| 5,755,693 A | 5/1998 | Walker et al. |
| 5,779,697 A | 7/1998 | Glowa et al. |
| 6,024,729 A | 2/2000 | Dehdashtian et al. |
| 6,083,207 A | 7/2000 | Heck |
| 6,106,487 A | 8/2000 | Duane et al. |
| 6,416,499 B2 | 7/2002 | Paul, Jr. |
| 6,551,283 B1 | 4/2003 | Guo et al. |
| 6,569,120 B1 | 5/2003 | Green et al. |
| 6,663,599 B2 | 12/2003 | Osbourne et al. |
| 6,712,791 B2 | 3/2004 | Lui et al. |
| 2001/0049499 A1 | 12/2001 | Lui et al. |
| 2002/0007152 A1* | 1/2002 | Hermann et al. ....... 604/167.04 |
| 2004/0054330 A1* | 3/2004 | Kurth et al. ................. 604/160 |
| 2005/0010238 A1* | 1/2005 | Potter et al. ................. 606/129 |

* cited by examiner

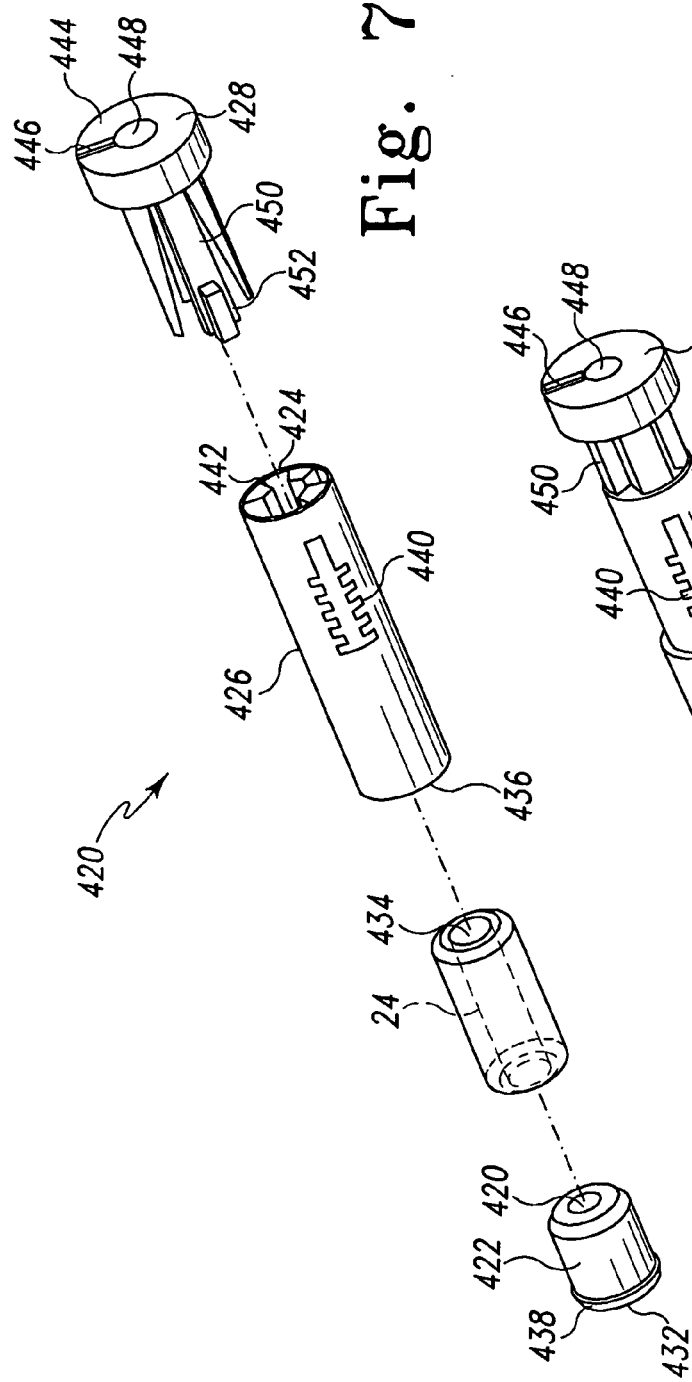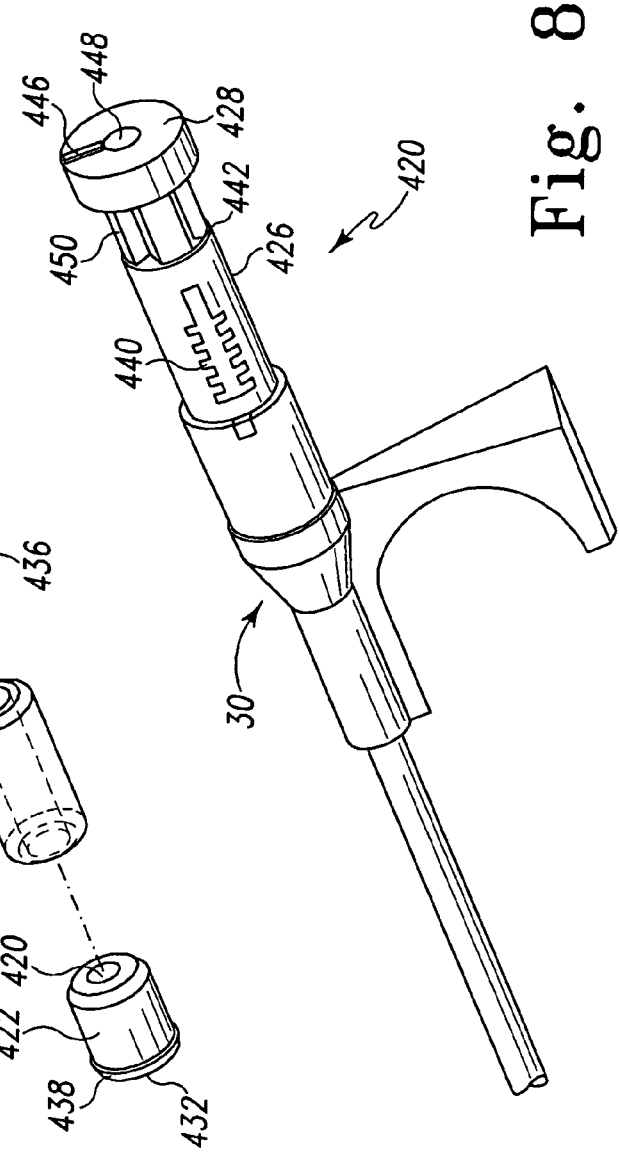

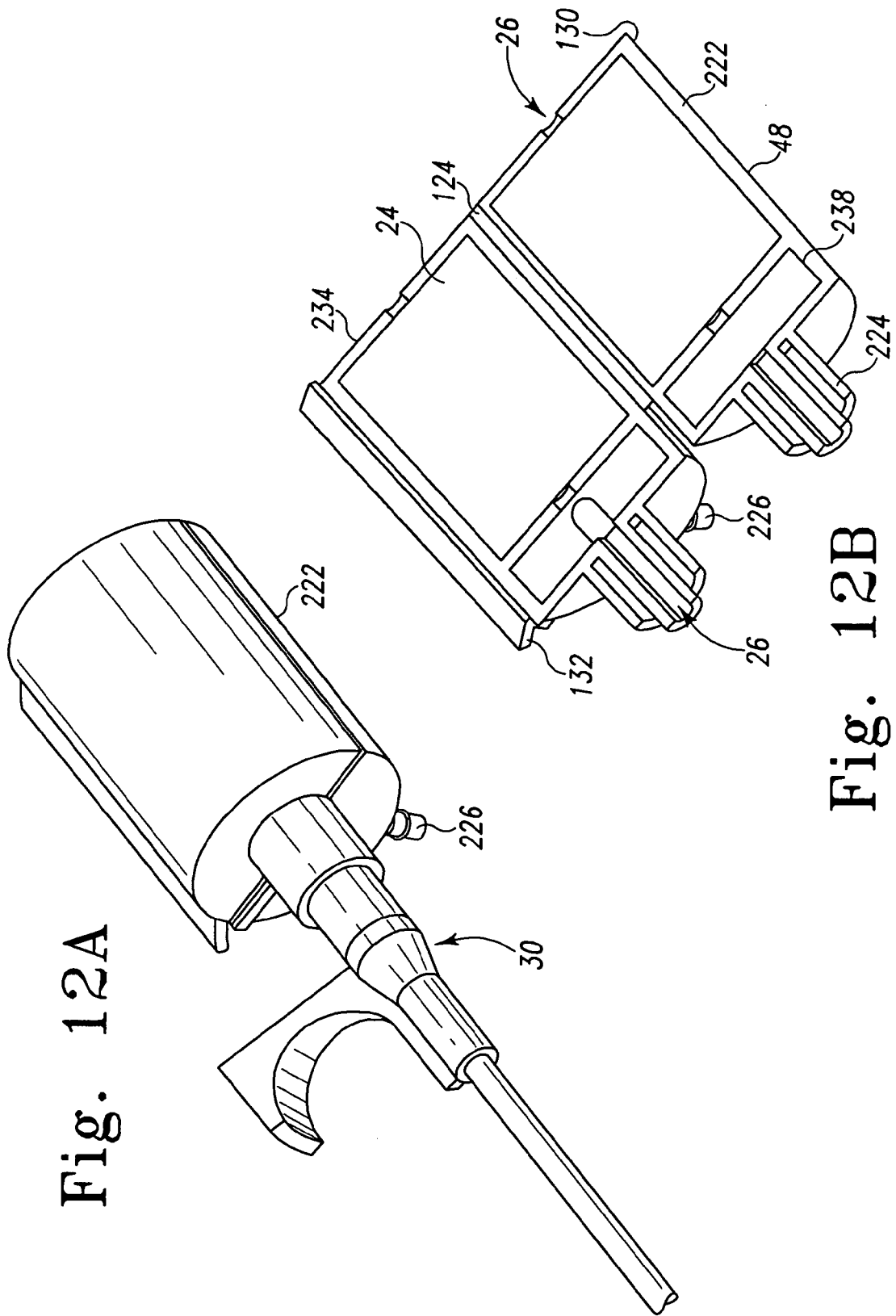

MODULAR HEMOSTATIC VALVE

CROSS-REFERENCE TO RELATED APPLICATIONS

This application is related to and claims all benefits of U.S. Provisional Applications Ser. No. 60/560,914 filed Apr. 9, 2004 and Ser. No. 60/573,659 filed May 21, 2004.

TECHNICAL FIELD

This invention relates to medical devices, in particular to hemostatic valves for intravascular devices.

BACKGROUND OF THE INVENTION

Percutaneous placement of intravascular catheters, pacemaker leads, etc. involves blood loss that, while easily controllable especially during venous access, can become significant during long procedures. For example, procedures such as placement of leads in the coronary sinus for biventricular pacing, can last 4 hours, during which time the blood loss of up to 500-600 cc can represent a risk to the patient. Additionally, the open conduit into the body can become a source of infection to the patient. To help reduce these potential risks, self-sealing hemostatic valves have been developed for use with introducer sheaths. These valves provide a seal against flashback of blood from the proximal end of the sheath, including when a second device is being manipulated within the introducer.

Medical devices with large proximal fittings, such as pacemaker leads and PICC lines, cannot be readily used through standard hemostasis valves and introducers because of the need to remove the introducer while leaving the other device in place. To address this need, splittable sheaths and hemostasis valves were developed so that the introducer and valve can be removed while the inner device remains in the patient. Combinational devices exist, such as the SAFE-SHEATH™ Splittable Valved Sheath System (Pressure Products, Inc., Rancho Palos Verdes, Calif.), which is comprised of a splittable valve attached to the end of a scored introducer sheath. The valve housing containing the valve membrane is split along scores lines, which are aligned with score lines that continue down the length of the integral introducer. Thus, the valve and introducer are split together. One disadvantage of this combinational system is the lack of flexibility in how the device is used. For example, to place a coronary sinus pacemaker lead, a physician will often wish to advance the long introducer sheath into the coronary vessel, then partially withdraw the sheath, perhaps 10 cm, prior to introducing the pacing lead. The large integral valve at the proximal end of the sheath cannot enter the patient, therefore, the physician must have an undesirably long section of introducer exiting the patient, where ideally, he or she would like to peel the introducer back closer to the entry site. In addition, the scored introducer portion of the SAFE-SHEATH™ lacks the structural integrity to negotiate tortuous bends of the coronary vessels. Because the valve and introducer are designed only to be used together, the system cannot be adapted to work with different sheaths and other intravascular devices that may offer important clinical advantages in certain procedures.

Furthermore, while a valve body shell may provide an adequate barrier against fluid backflow when used in the venous system where pressures typically average around 0.2 psi, arterial pressures represent over a ten fold increase over that of the venous side, making sealing much more difficult.

What is needed is a simple system that provides a platform to introduce materials to the body and offers quick disembling capabilities. It is desirable to have a valve that can provide superior sealing characteristics, especially in the presence of high backflow pressures such as seen in arterial applications. It is also desirable to prevent leakage of fluids and/or reduce exposure to air-borne pathogenic organisms. Further considerations include having a splittable hemostatic valve of simple construction that is easy to use, functional and inexpensive to manufacture.

SUMMARY OF THE INVENTION

The foregoing problems are solved in a modular hemostatic valve that is quickly removable with a longitudinally extending sealing element and an interfacing region sized and configured to permit the valve to be coupled to a lead, a separate introducer sheath or other tubular medical device to permit passage of a catheter or device therethrough with minimal blood flashback.

According to one aspect of the invention, the modular hemostatic valve may include a valve body made of two unconnected semi-cylindrical shells. When closed, the two shells may form an elongated hollow passageway therewithin. The shells may be made of silicone or another elastic material that allows the valve body to be fitted into an introducer sheath while offering some sealing characteristics. The distal end of the valve body may be closed around an end lead. Subsequently, the end lead may be placed into the introducer sheath, such as a PEEL-AWAY® Introducer Sheath (COOK Incorporated, Bloomington, Ind.). While typically, a dilator is initially co-introduced, followed by the device being placed, such as a pacemaker lead or intravenous catheter having a large proximal hub or fitting. The valve body may be split open and removed from the introducer sheath, which may also be split apart, leaving the indwelling device undisturbed.

According to another aspect of the invention, the valve body may be made of two semi-cylindrical shells connected by a living hinge. When closed, the shells may form an elongated hollow passageway therewithin. The proximal end of the introducer sheath may be inserted into the modular hemostatic valve to form a double seal. Simultaneously, a small square protrusion at the proximal end of the introducer sheath may be slid into a guild and locking channel at one end of the valve body to ensure structural integrity of the valve.

According to a further aspect of the invention, the end lead may be made of two splittable halves. The distal portion of the end lead may include a cylindrical extension for inserting into a proximal hub of the introducer sheath. The end lead distal portion may be barbed for a tighter fit. The proximal portion of the end lead may have an annular space for receiving the distal end of the valve body such that sandwiching contact surfaces of the valve body may form a double seal with the annular space of the end lead. Another end lead may be used to seal the proximal end of the valve body in the same way as the first end lead.

According to another aspect of the invention, the sealing element may be provided within the passageway of the modular hemostatic valve. The sealing element may be separately formed and affixed within the valve body passageway. This sealing element, which provides an additional blood barrier, may include silicone, foam, gel, or virtually any biocompatible material that may provide a seal around a first medical device being passed through the modular hemostatic valve. The sealing element may be a solid cylindrical column or may include slits or apertures to allow passage of the first medical device. The sealing element may also be composed of two longitudinally extending semi-cylindrical members, which may come together when the valve body shells are closed. In this configuration, each member of the sealing element may contain a slight interior bulge for better seal. The sealing element may remain attached to the valve body shell when the modular hemostatic valve is split open and removed.

According to a further aspect of the invention, the modular hemostatic valve may include a stopper, a sealing element, a body shell, and a plug. The stopper and the sealing element may be axially arranged within the body shell with the stopper placed closer to the distal end of the body shell. The plug may be inserted into the body shell at the proximal end of the body shell. The plug may include a longitudinal adjustment feature that permits the plug to squeeze the sealing element onto a medical device being passed through the modular hemostatic valve.

According to another aspect of the invention, the valve body may be made of three or more shell segments, each segment preferably being connected to at least one adjacent segment by a living hinge. When closed, the shell segments preferably form an elongated hollow passageway for receiving a sealing element. The proximal end of the introducer sheath may be inserted into the modular hemostatic valve to form a double seal. Simultaneously, a small square protrusion at the proximal end of the introducer sheath may be slid into a guild and locking channel at one end of the valve body to ensure structural integrity of the valve.

According to a further aspect of the invention, the valve body may include a first engaging member and a second engaging member on each of the top half and bottom half of the valve body along the passageway. The first engaging member and the second engaging member are designed to permit the first medical device to pass through the passageway while simultaneously exert friction to the first medical device to prevent slippage.

BRIEF DESCRIPTION OF THE DRAWINGS

FIG. 7 depicts a perspective view of a dissembled modular hemostatic valve having four components to be combined axially.

FIG. 8 depicts a perspective view of an assembled modular hemostatic valve having four components combined axially.

FIG. 12A depicts another perspective view of the modular hemostatic valve shown in FIG. 11A.

FIG. 12B depicts another perspective view of the modular hemostatic valve shown in FIG. 11B.

DETAILED DESCRIPTION

Figures 1, 2:
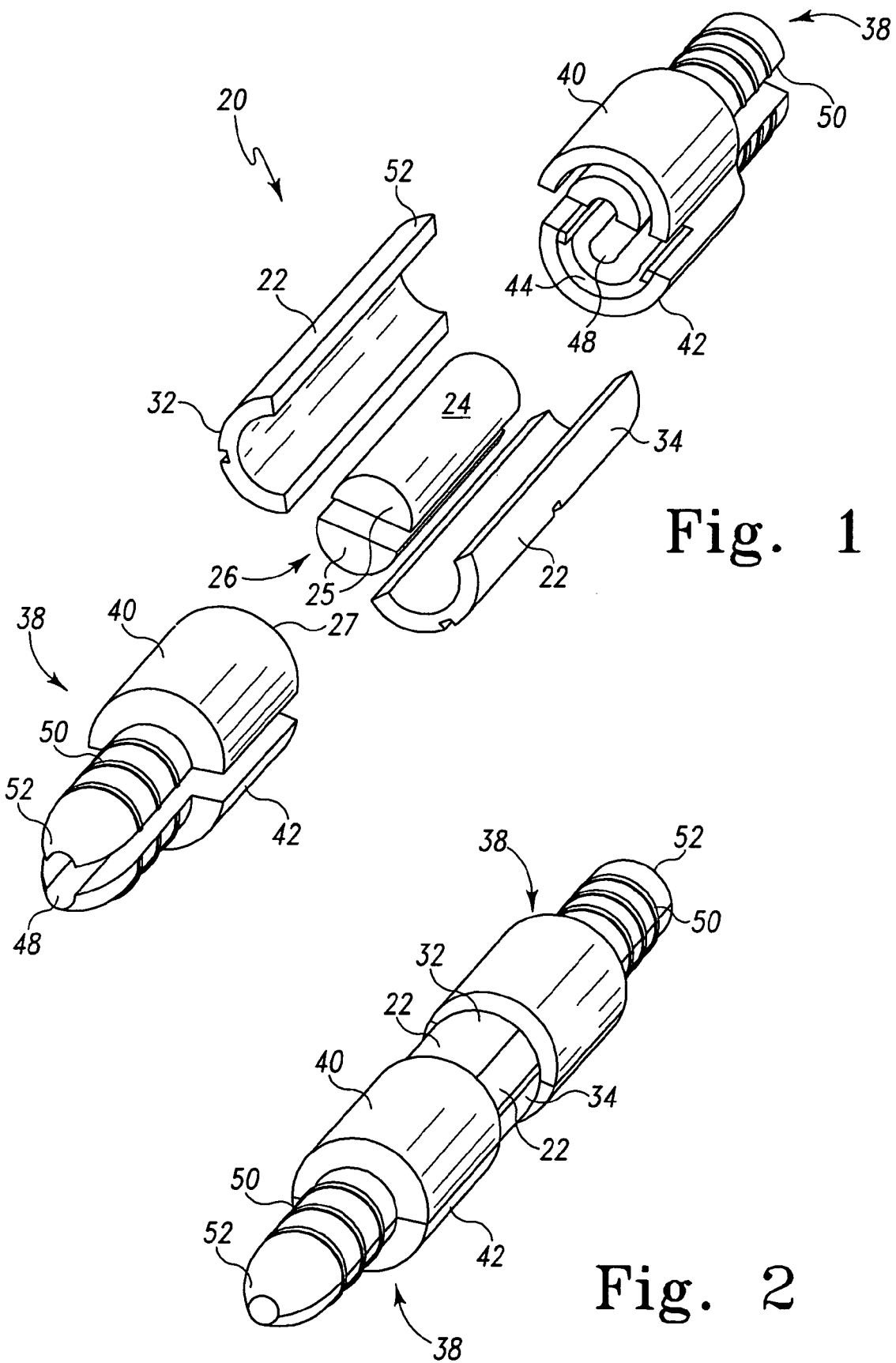
FIG. 1 depicts a perspective view of a dissembled modular hemostatic valve to be closed around two end leads in accordance with the present invention.
FIG. 2 depicts a perspective view of an assembled modular hemostatic valve closed around two end leads.

A better understanding of the present invention will now be gained upon reference to the following detailed description, when read in conjunction with the accompanying drawing, wherein like reference characters refer to like parts throughout the several views and different embodiments of the present invention.

A first embodiment of a modular hemostatic valve 20 of the present invention is shown in FIGS. 1 and 2 to include a splittable valve body 22 and a sealing element 24. The splittable valve body 22 defines a passageway 26, which is configured to house the sealing element 24. The sealing element 24 is configured to facilitate the passage of a first medical device, and the splittable valve body 22 is configured to engage a second medical device. The first medical device can be typically a catheter, dilator, or pacemaker lead, while the second medical device can be typically a tubular medical conduit such as a splittable introducer sheath.

The modular hemostatic valve 20 can substantially prevent or eliminate the leakage or flashback of blood or other bodily fluids. It should be noted that the modular hemostatic valve 20 has possible applications in other types of non-vascular procedures where there is a desire to prevent leakage of fluids and/or reduce exposure to air-borne pathogenic organisms. For example, the modular hemostatic valve 20 can be used in minimally invasive neurological procedures to limit contact of the cerebral spinal fluid with ambient air. Another possible application would be urological procedures where modular hemostatic valve 20 could help prevent the introduction of pathogenic organisms into the urinary tract.

In the first embodiment, the splittable valve body 22 preferably includes a first shell 32 and a second shell 34 connected to the first shell 32 to form the passageway 26. Preferably, the first 32 and second shells 34 are semi-cylindrical hollow shells, although other shapes may be used. The splittable valve body 22 can be split open manually by disconnecting the first shell 32 and the second shell 34 into two separate pieces and exposing the passageway 26. Silicone, which provides superior sealing characteristics, can be used to make the splittable valve body 22 in the preferred embodiment, although it is within the scope of the invention for the splittable valve body 22 to include a rigid or semi-rigid plastic or another non-elastic material.

In the first embodiment, the modular hemostatic valve 20 also includes a splittable end lead 38, as depicted in FIGS. 1 and 2. The splittable end lead 38 can be subsequently inserted into a medical conduit at some point prior to or during the procedure involving the tubular medical conduit. The splittable end lead 38 includes a first half member 40 and a second half member 42 connected to the first half member 40 to define a receiving chamber 44. The receiving chamber 44 is configured to capture an end 46 of the splittable valve body 22. The splittable end lead 38 also includes a coupling component 48 that is in fluid communication with the passageway 26 and allows a medical device (not shown) to pass therethrough when the splittable end lead 38 engages the splittable valve body 22. The splittable end lead 38 further includes a barbed lead 50 that is configured to engage a medical conduit or other medical device (not shown). In the preferred embodiment, the modular hemostatic valve 20 includes splittable end leads 52 on both ends of the splittable valve body 22.

The splittable end lead 38 can be split open manually by disconnecting the first half member 40 and the second half member 42 into two separate pieces and exposing the receiving chamber 44. After separating the splittable end lead 38, the splittable valve body 22 can also be split open manually by disconnecting the splittable valve body shells 32 and 34 and exposing the passageway 26 and the sealing element 24. The sealing element can be subsequently split into first 25 and second members 27 as desired.

Figure 15:
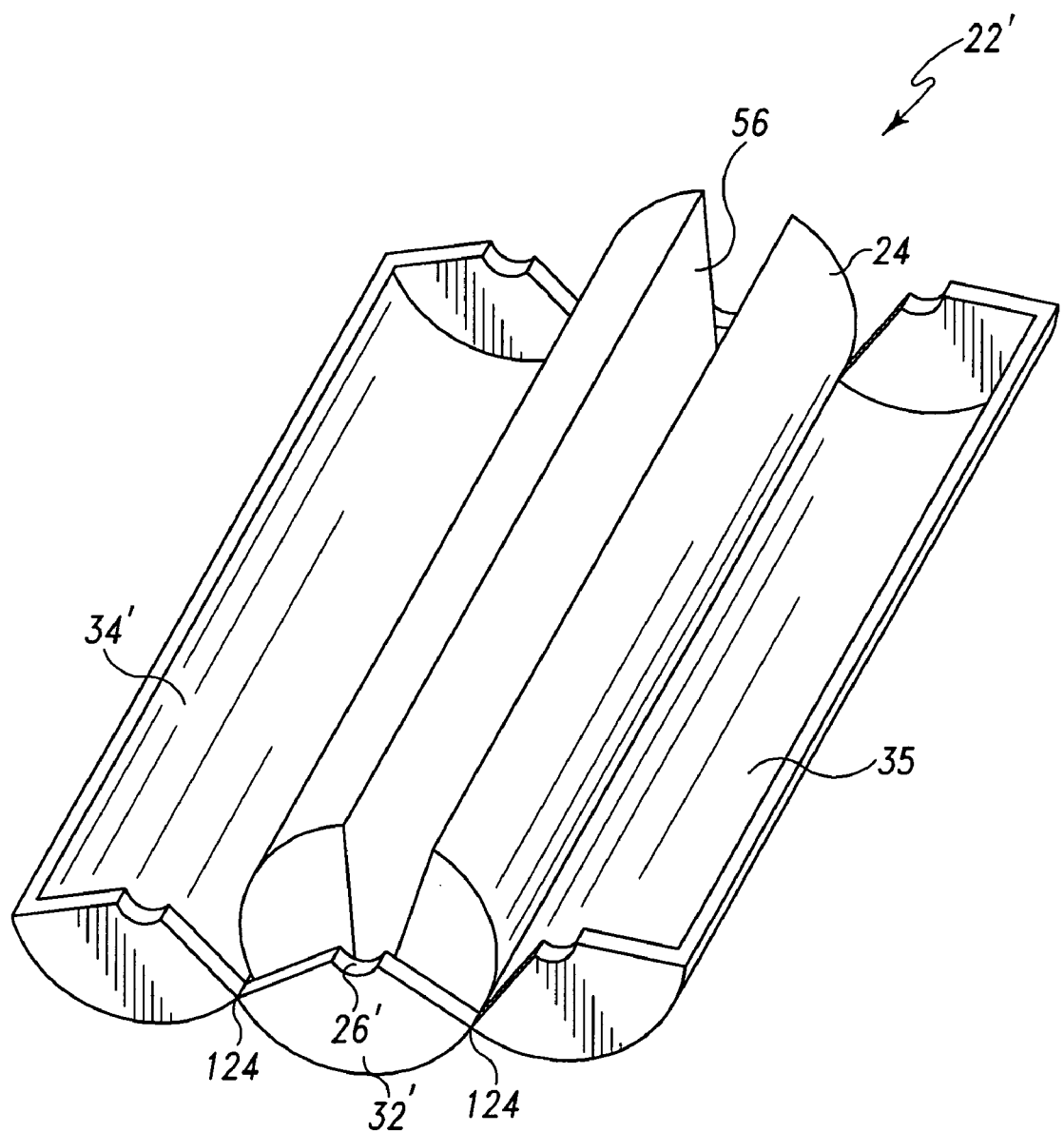
FIG. 15 depicts a perspective view of a modular hemostatic valve in three partial-cylindrical longitudinally extending members connected by a living hinge and having a sealing element including a slot opening.
Figure 16:
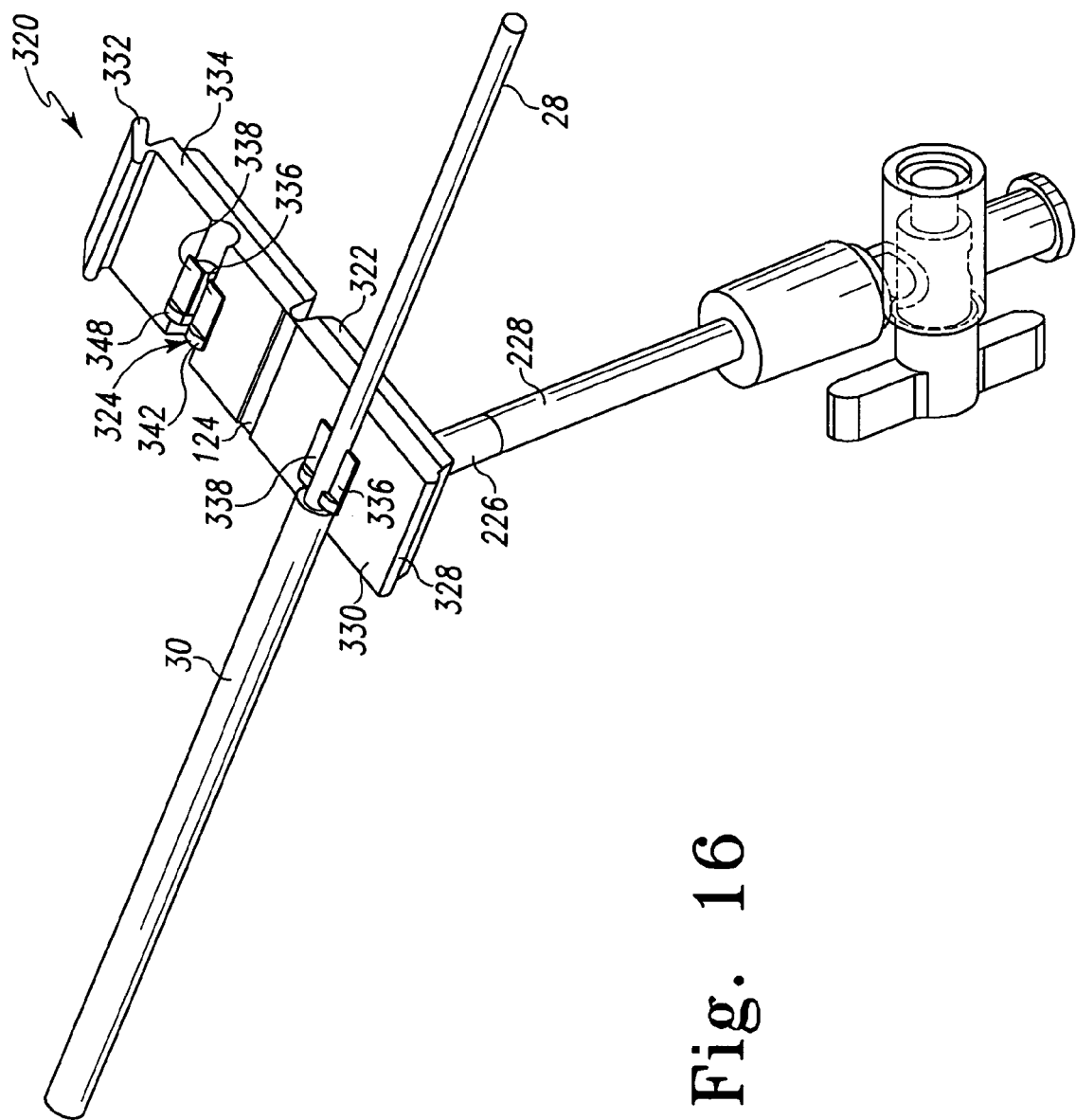
FIG. 16 depicts a perspective view of an opened modular hemostatic valve having a first engaging member and a second engaging member engaging a first medical device.

FIG. 15 depicts an alternative embodiment for the splittable valve body 22 previously discussed. The alternative splittable valve body 22' can include a first shell 32', a second shell 34' connected to the first shell 32', and a third shell 35 connected to the first shell 32' and the second shell 34' to form the passageway 26'. It is noted that the first shell 32', the second shell 34' and the third shell 35 can be connected by living hinges 124. While the splittable valve body 22' is depicted to be formed of three members 32', 34' and 35, the number of members is not limited, and the splittable valve body 22' could be formed of four or more partial-cylindrical longitudinally extending members.

Figure 9:
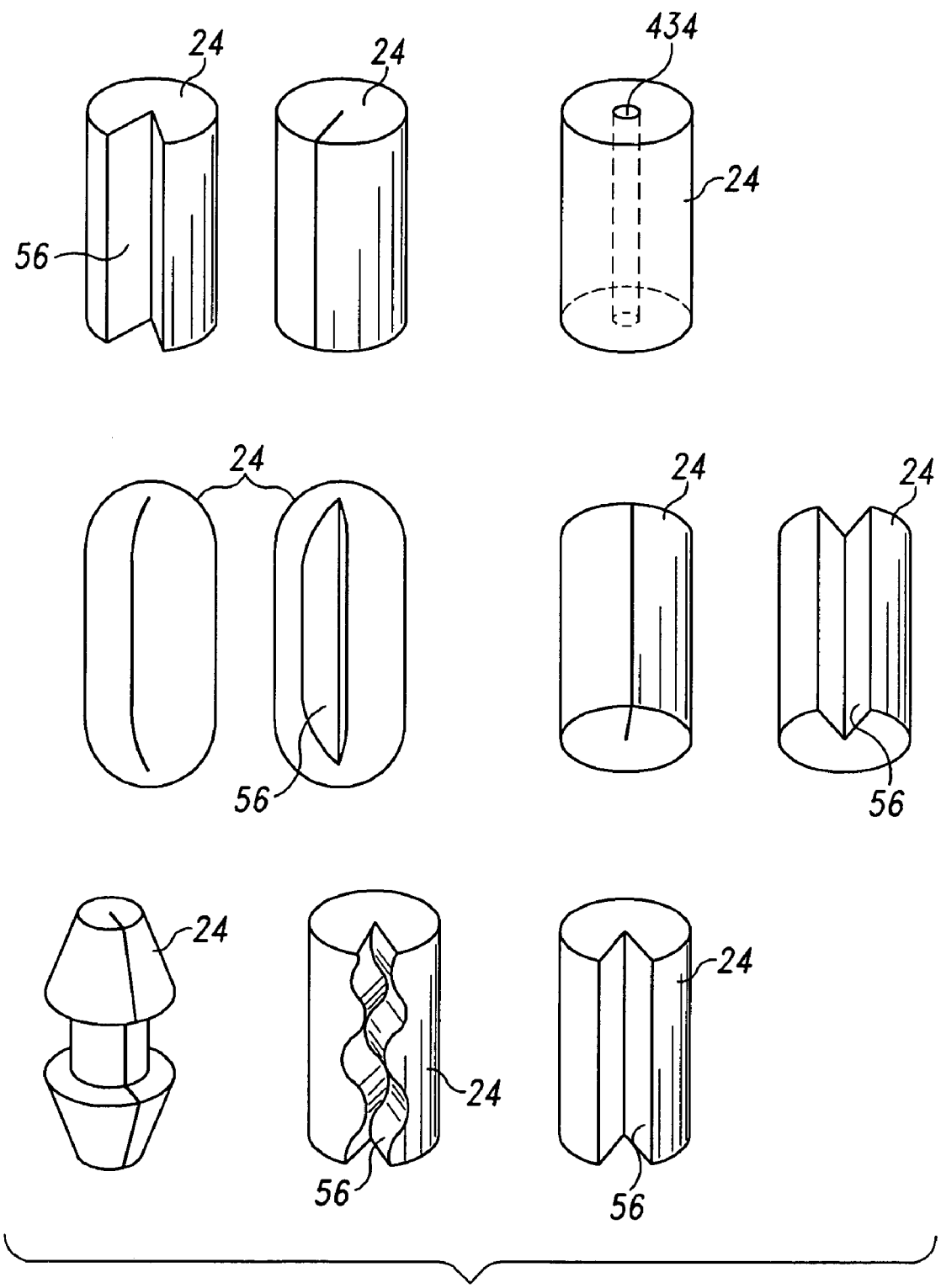
FIG. 9 depicts a variety of possible shapes for a sealing element to be employed as a modular hemostatic valve of the present invention.

Having modular hemostatic valve 20 with superior sealing characteristics is important, especially in arterial applications, when the backflow pressures are high. Lying within the passageway 26 of the modular hemostatic valve 20 is the sealing element 24, placed to provide an additional blood barrier. In the first embodiment, the sealing element 24 includes a first member 25 and a second member 27 contacting the first member 25 to form a longitudinally extending sealing insert, as depicted in FIG. 1. The sealing element 24 can be separately formed from the splittable valve body 22, configured to be inserted into the passageway 26 and affixed with silicone adhesive or otherwise secured in place. It is noted that other shapes may be used, such as a pill-shaped, plug-shaped with seal rings or seams, solid with ripples inside, as depicted in FIG. 9. Moreover, the sealing element 24 can include a slit 56 to ease the passage of the first medical device 28, as depicted in FIG. 9. In the preferred embodiment, the slit 56 is preformed through the sealing element 24 to permit through passage of a dilator shaft being introduced through first medical device 28 for placement at the target site. Other examples include solid with a hole, slit with larger opening, etc.

The sealing element 24 can include any biocompatible material capable of producing hemostasis and allowing passage of the first medical device 28 therethrough. In the preferred embodiment, the sealing element 24 is made of silicone foam. Other possible materials include, but are not limited to, a viscous liquid, such as glycerin; a gel; a foam (such as silicone); a sponge material; densely packed solid particles such as minute beads or fibrous material; and strips of material such as collagen. Collagen and other certain other materials are able to absorb and retain blood providing an additional mechanism of protection. Materials can be used in combination, for example, a gel-impregnated foam or collagen sponge.

Figure 4:
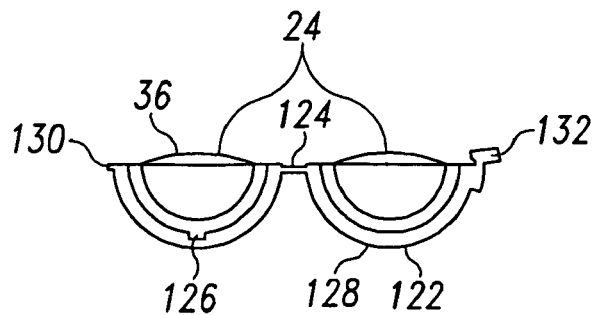
FIG. 4 depicts a front elevation view of a modular hemostatic valve connected by a living hinge and having a sealing elements with a slight interior bulge.
Figure 3:
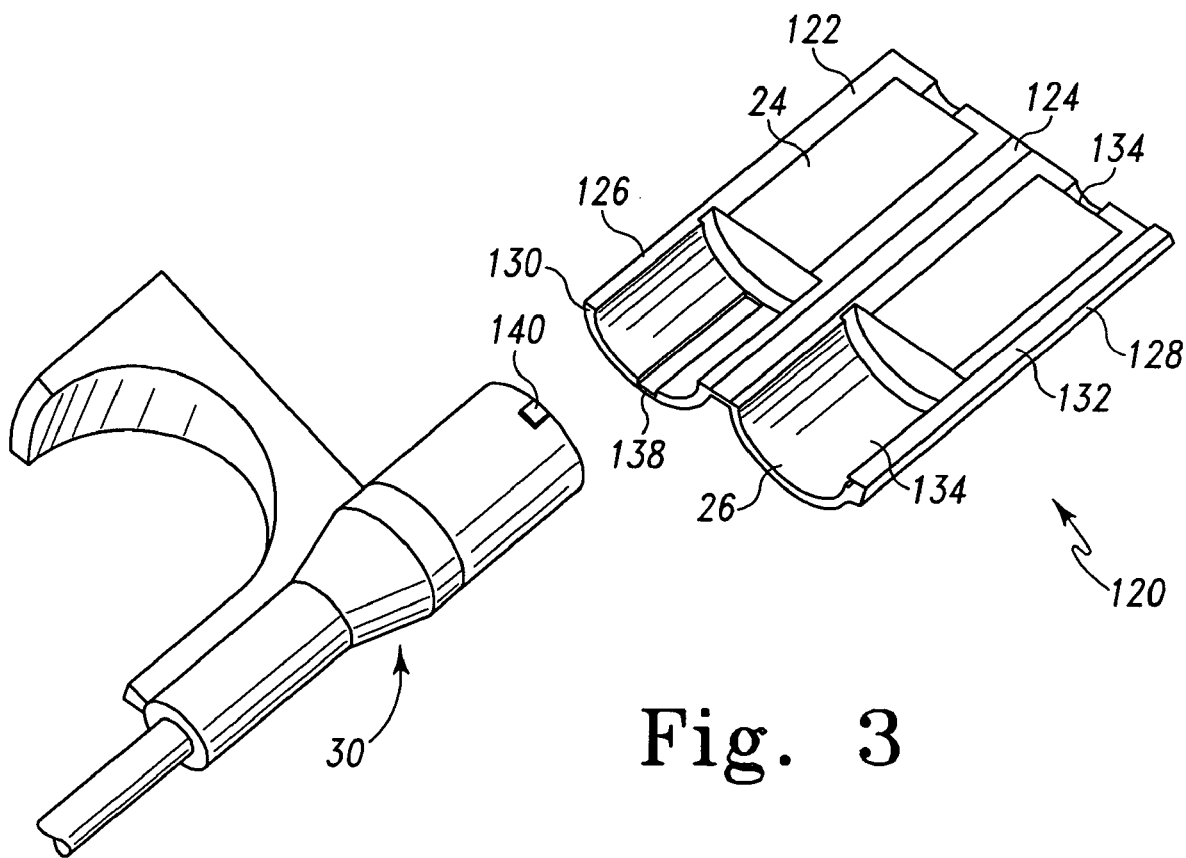
FIG. 3 depicts a perspective view of a modular hemostatic valve connected by a living hinge and having sealing elements in two semi-cylindrical longitudinally extending members.

In a second embodiment, as depicted in FIGS. 3 and 4, the modular hemostatic valve 120 includes a splittable valve body 122 and the sealing element 24. The spliftable valve body 122 defines the passageway 26 and is configured to house the sealing element 24. The sealing element 24 is configured to facilitate the passage of the first medical device (not shown), as noted before, and the splittable valve body 122 is configured to engage a second medical device 30.

In this embodiment, the splittable valve body 122 includes a living hinge 124 attaching the first shell 126 and the second shell 128. The first shell 126 also includes an elongated protrusion 130, and the second shell 128 further includes a coupling hub 132 for capturing the elongated protrusion 130. In the preferred embodiment, the splittable valve body 122 includes a small aperture 134 to facilitate smooth passage of a relatively large-diameter first medical device 28 therethrough. Also in this embodiment, the sealing element 24 can include two semi-cylindrical inserts integrally attached to the splittable valve body 122. Each of the inserts can include a slight bulge 36 to provide a better seal when the splittable valve body is closed, as depicted in FIG. 4.

The splittable valve body 22 further defines an interfacing region 134 configured to capture the second medical device 30. To secure the splittable valve body 122 to the second medical device 30, the splittable valve body 122 can include a guide track 138 to couple with a corresponding protrusion 140 on the second medical device 30 in one example.

Figure 5:
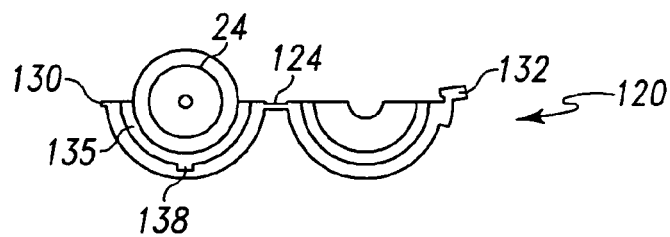
FIG. 5 depicts a perspective view of a modular hemostatic valve connected by a living hinge and having a sealing element in a longitudinally extending member.
Figure 6:
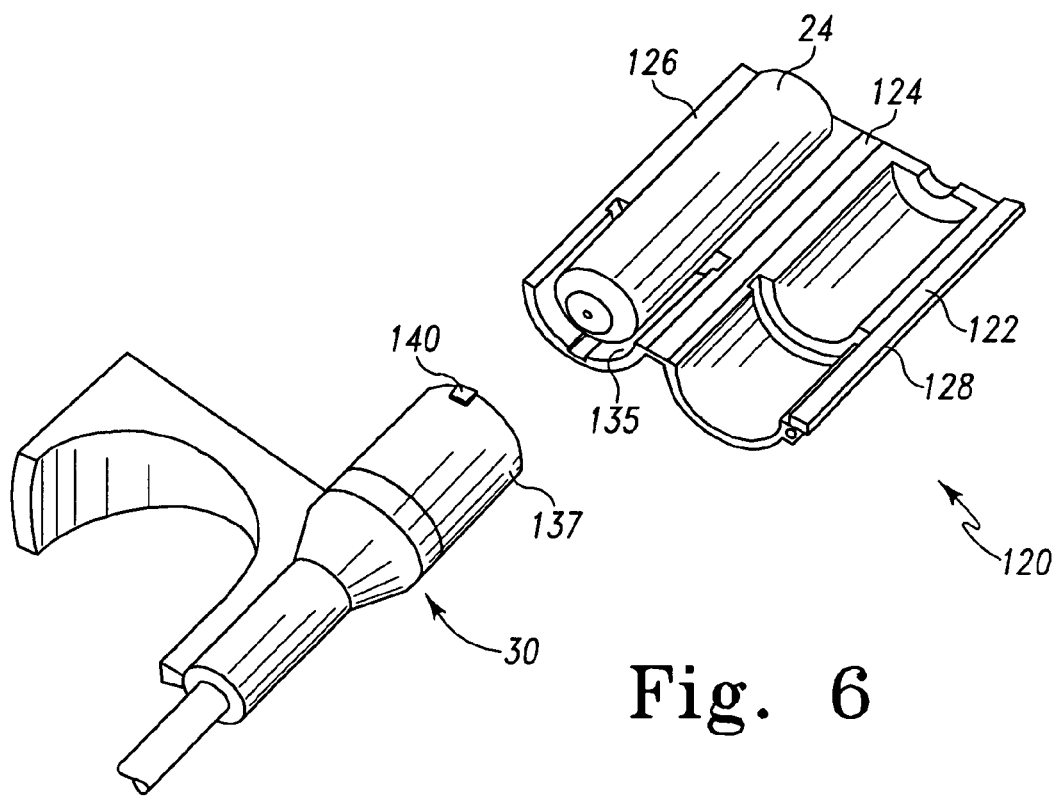
FIG. 6 depicts a front elevation view of a modular hemostatic valve connected by a living hinge and having a sealing element in a longitudinally elongated member.

A slight variation in the second embodiment can be seen in FIGS. 5 and 6, where the annular space 135 between the splittable valve body 122 and the sealing element 24 define the interface region 134 that is configured to capture an end 137 of the second medical device 30 to form a double seal. The sealing element 24 is a cylindrical tube integrally attached to the splittable valve body 122 having a slit 56 for the first medical device (not shown) to pass through. The double seals are particularly advantageous when used with the second medical device 30 such as the ATTAIN™ Coronary Sinus Introduction Sheath (Medtronic Inc., Minneapolis, Minn.). This configuration enables the splttiable valve body 122 to remain closed during use while offers quick dissembling capability and allow external access along the length of the passageway 26 after use. When being removed, the splittable valve body first 126 and second shells 128 will fall away in one piece from any medical device passing through the splittable valve body 122. The splittable valve body first 126 and second shells 128 will remain attached to each other by the living hinge 124.

In a third embodiment, as depicted in FIGS. 10-14, the modular hemostatic valve assembly 220 includes a splittable valve body 222 with the passageway 26, and a sealing element 24 configured to traverse the passageway 26, similar to that shown in FIGS. 3-6. The splittable valve body 222 includes an interfacing region 224 to capture the second medical device 30. The splittable valve body 222 also includes a side port 226 that communicates with the passageway 26. The side port 226 can be used for a variety of purposes, for example, slow-drip intravenous administration. A length of tubing 228 can be attached to the side port 226 that, in turn, can include a luer lock port or similar-type fitting 230 to connect with a stop cock valve 232 or an I.V. line at the end distal to the patient. The side port 226 would be available to perform other functions such as infusion of medicaments, saline for flushing, or contrast media. The side port 226 could also be used to evacuate air from the system. The side port 226 is depicted as a nipple over which the tubing 228 is attached; however, other embodiments are possible such as a luer or other fitting, or merely an aperture into which the tubing 228 is inserted.

Figure 11A:
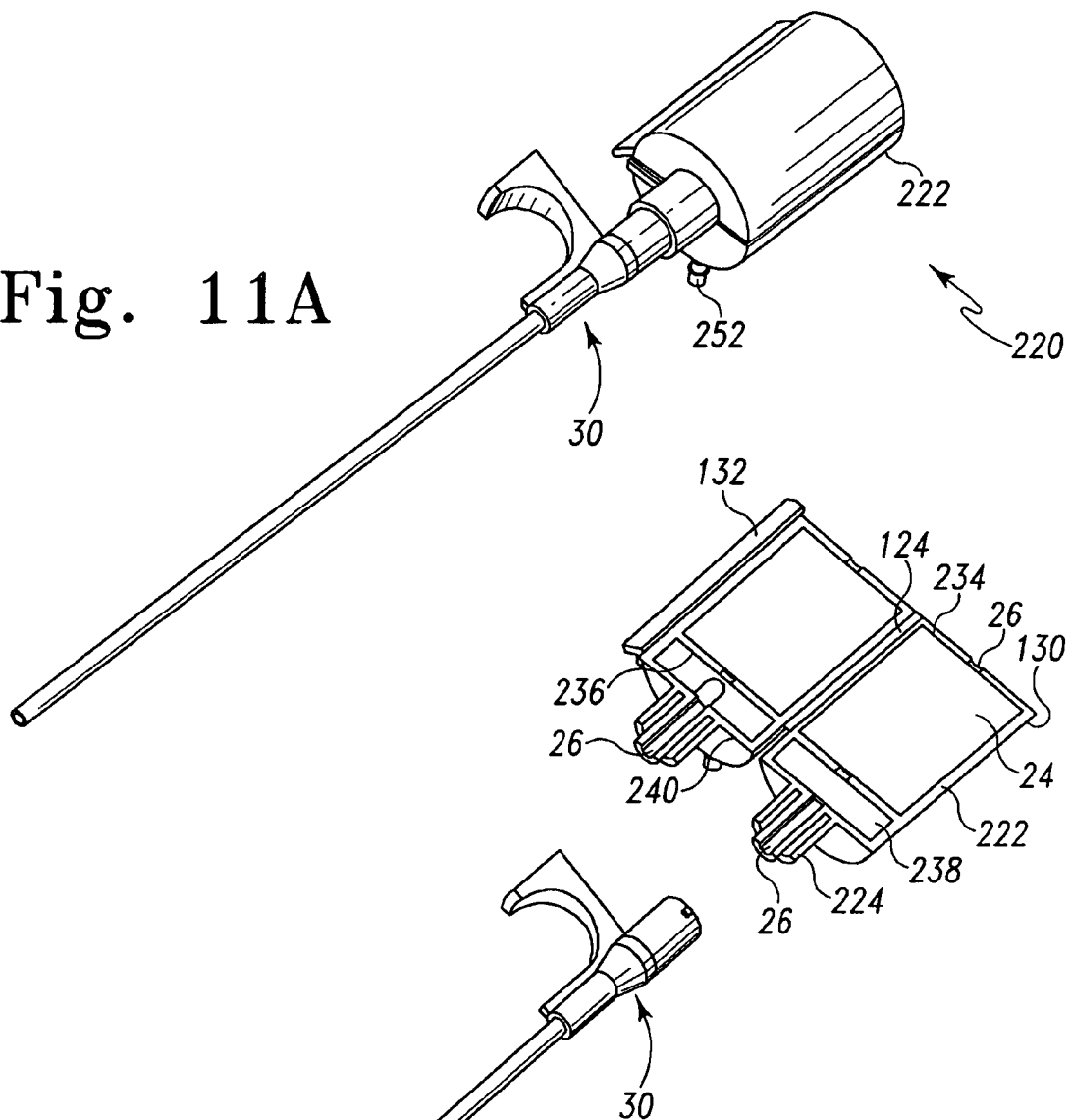
FIG. 11A depicts another perspective view of the modular hemostatic valve shown in FIG. 10 including the side port.
Figure 11B:
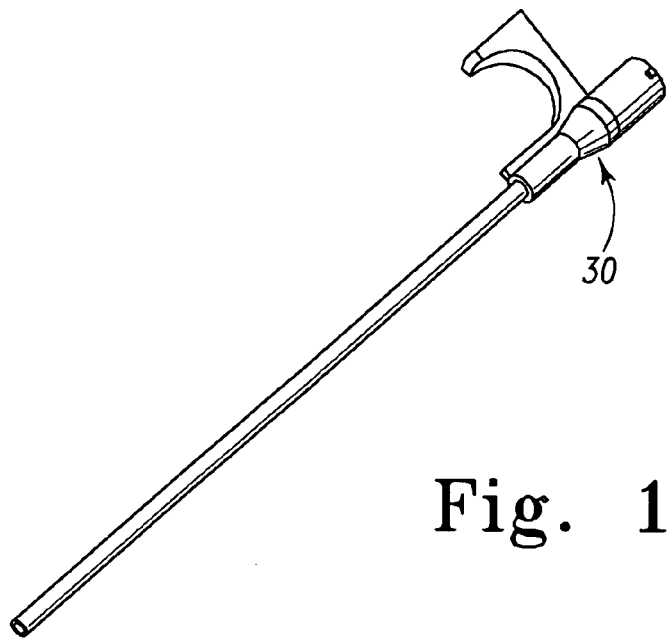
FIG. 11B depicts another perspective view of the modular hemostatic valve shown in FIG. 10 further dissembled to reveal primary and secondary sealing elements.
Figure 13:
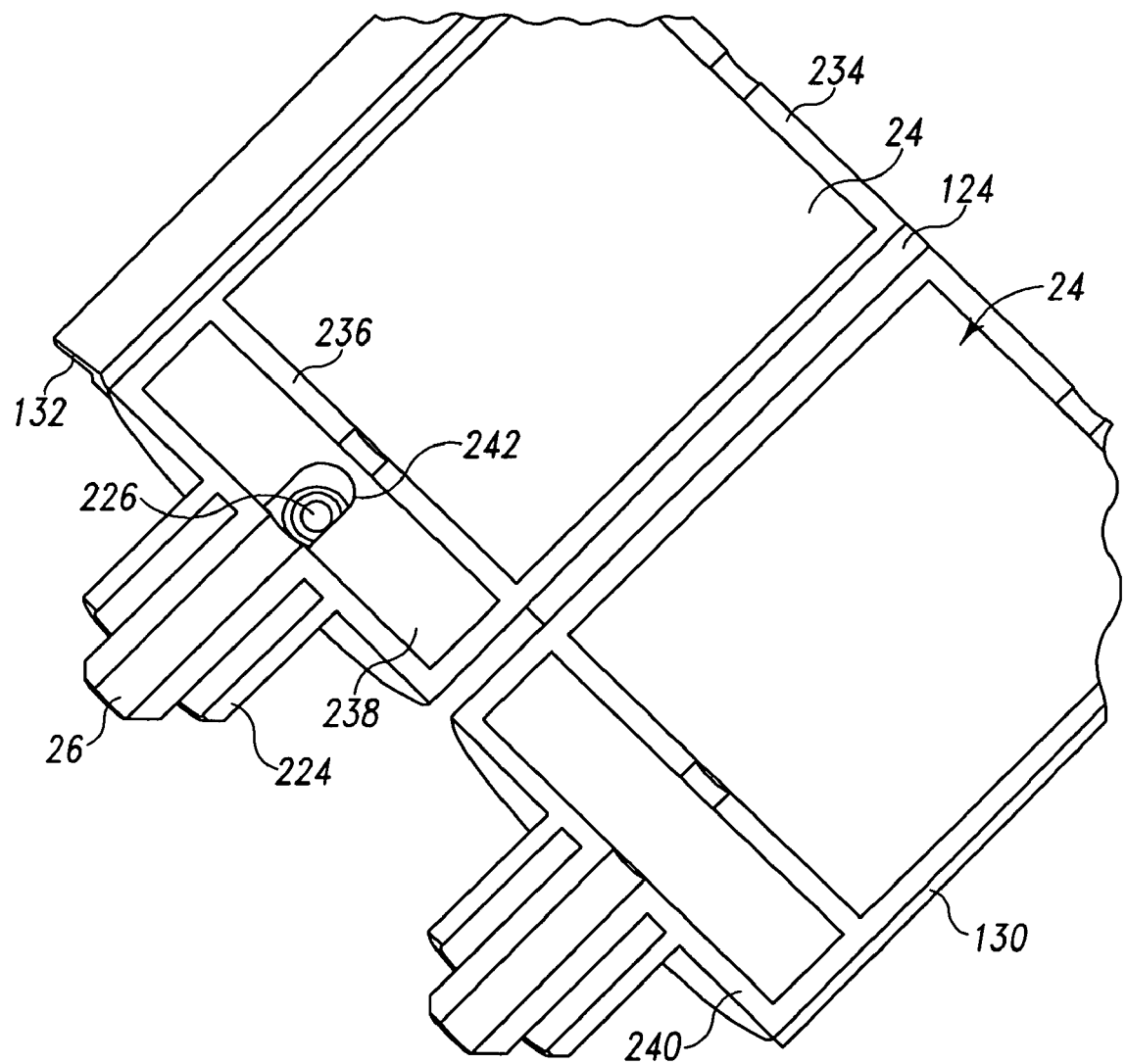
FIG. 13 depicts a close-up perspective view of the modular hemostatic valve shown in FIG. 10 showing the interior of the side port.
Figure 14:
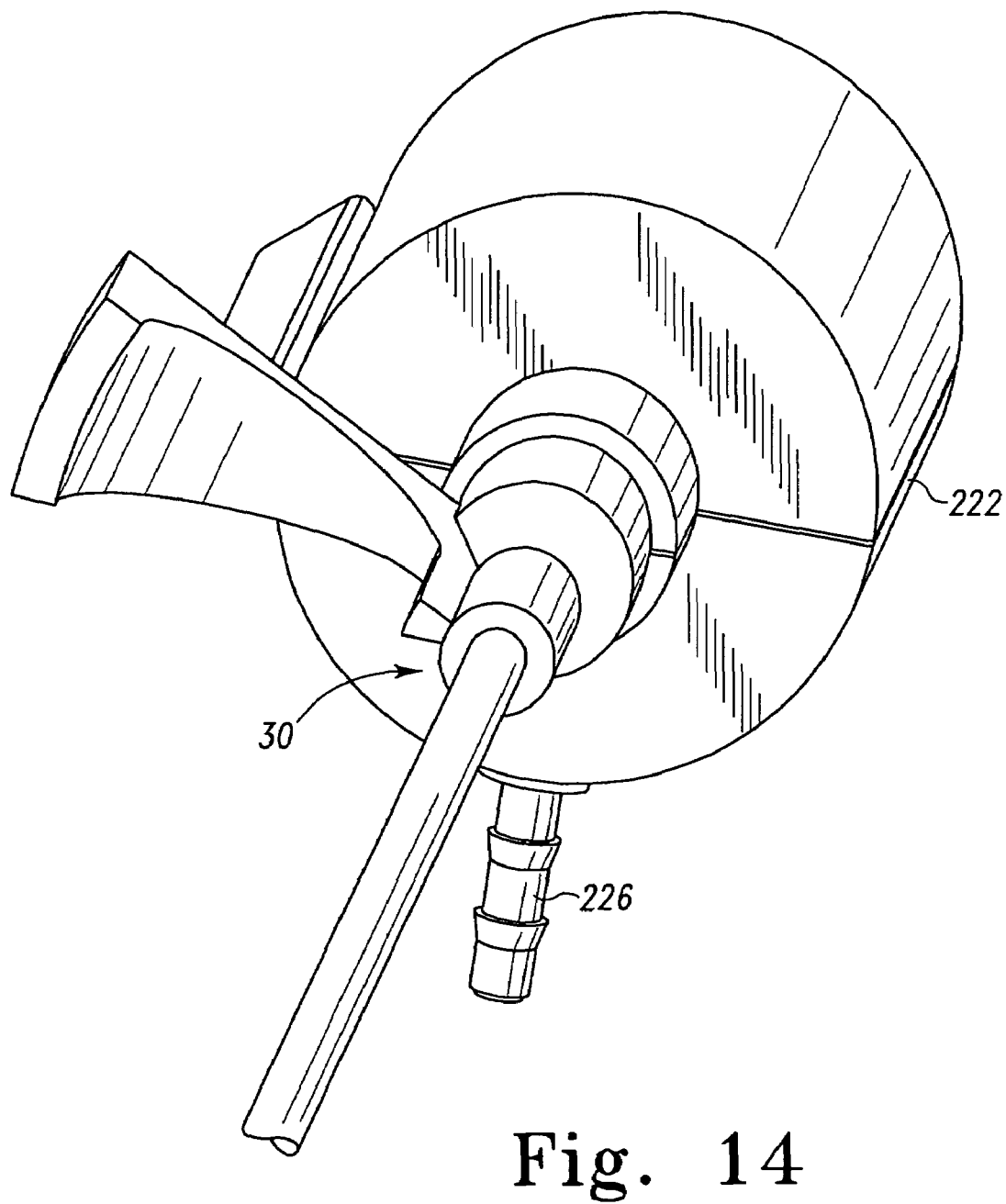
FIG. 14 depicts a close-up perspective view of the modular hemostatic valve shown in FIG. 12A, but from a different perspective.

As shown in FIGS. 11B, 12B, and 13, the splittable valve body 222 is seen to include a primary sealing element 24 disposed between the proximal end 234 of the valve assembly and an intermediate wall 236. A secondary sealing element 238 is situated between the intermediate wall 236 and the distal end 240 of the splittable valve body 222. The primary sealing element 24 and secondary sealing element 238 can have differing characteristics and compositions. The secondary sealing element 238 is shown to be longitudinally much shorter than the longitudinally elongated primary sealing element 24. It will be noted from FIG. 13 that the secondary sealing element includes a lateral groove 242 leading to the side port 226. The elements of splittable valve body 222 not specifically discussed here have the same features and functions as the corresponding elements identified by corresponding reference numerals in the previously discussed embodiments.

Figure 17:
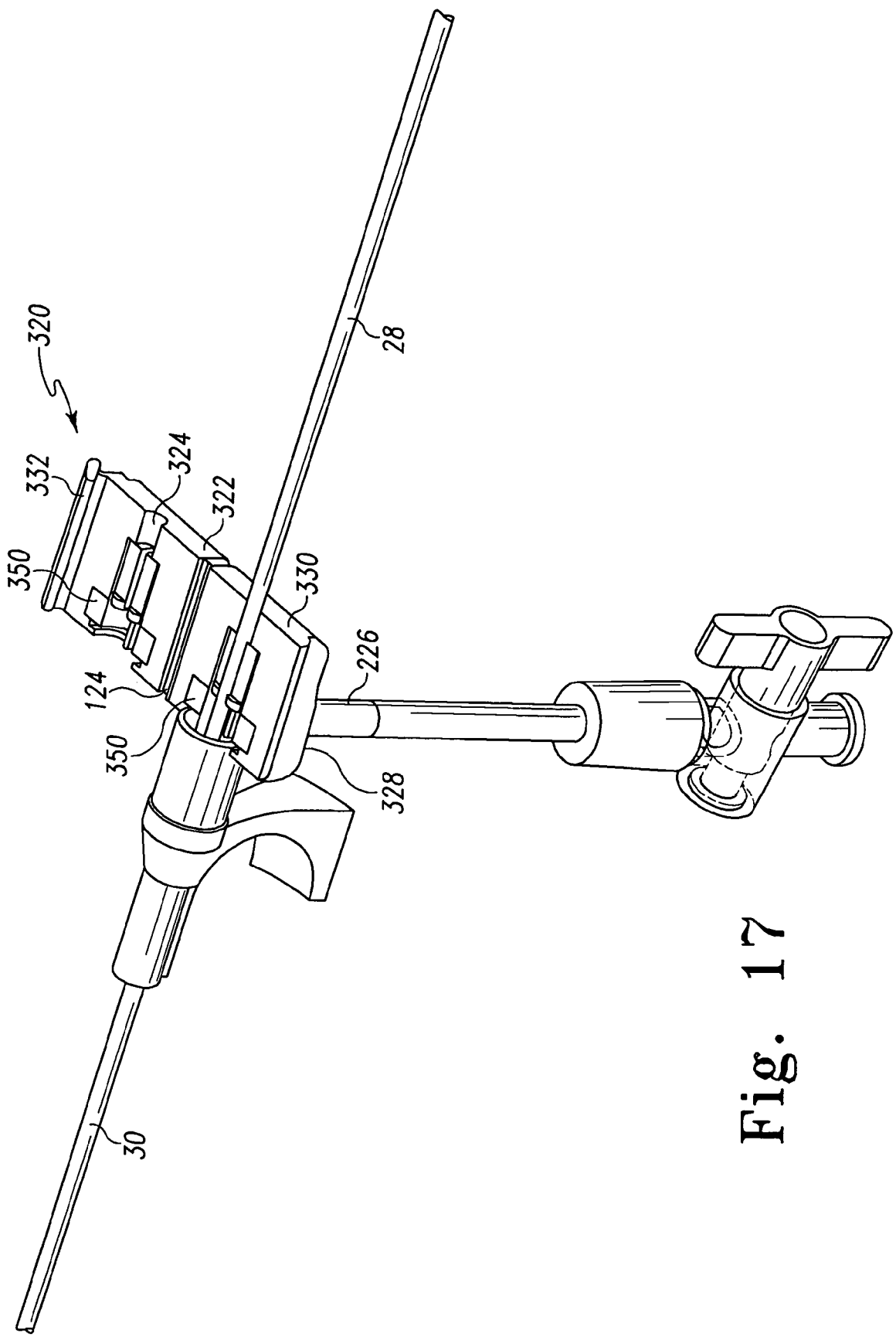
FIG. 17 depicts a perspective view of FIG. 16 with a second medical device.
Figure 18:
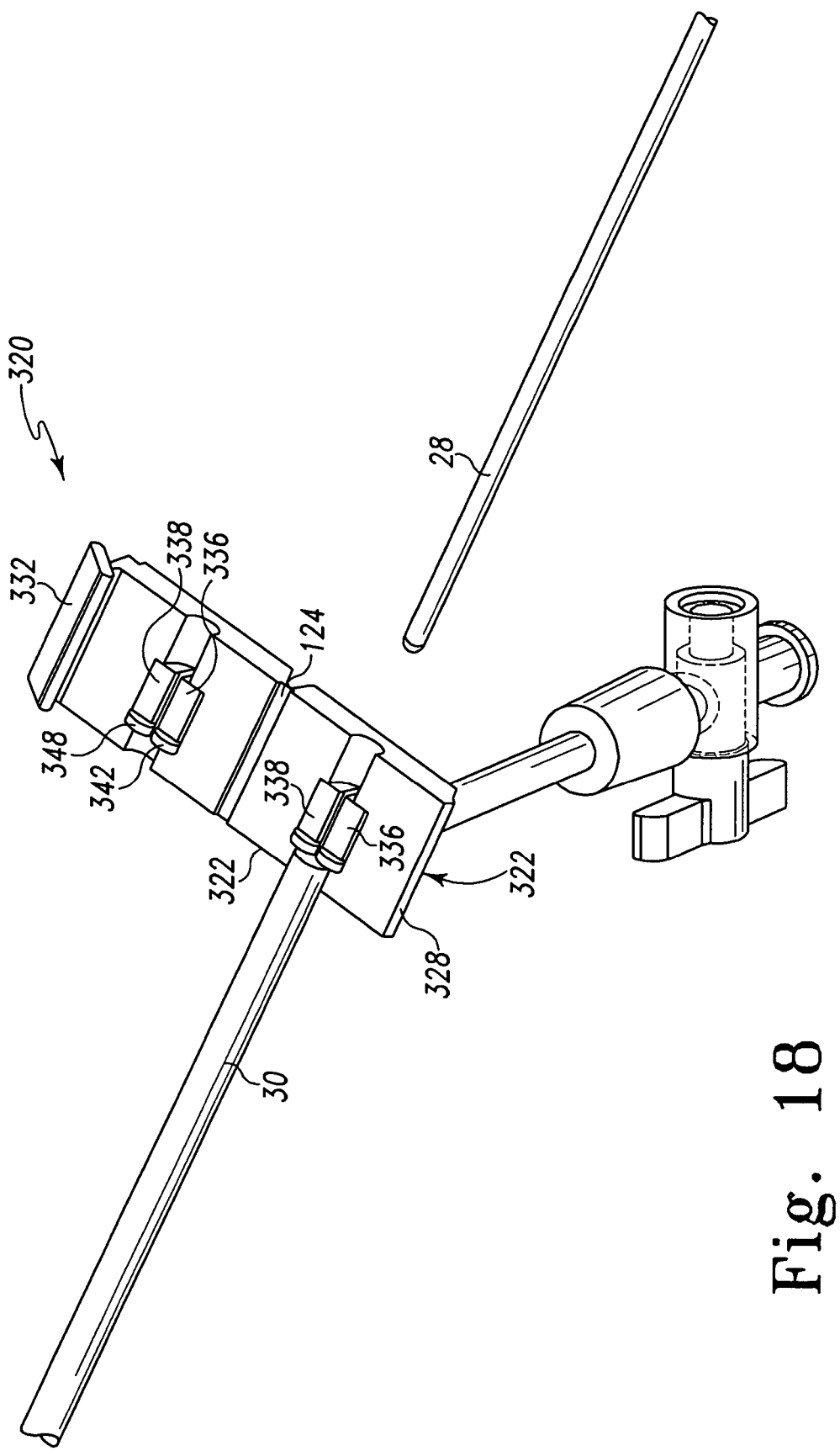
FIG. 18 depicts a perspective view of FIG. 16 with the first medical device disengaged.
Figure 19:
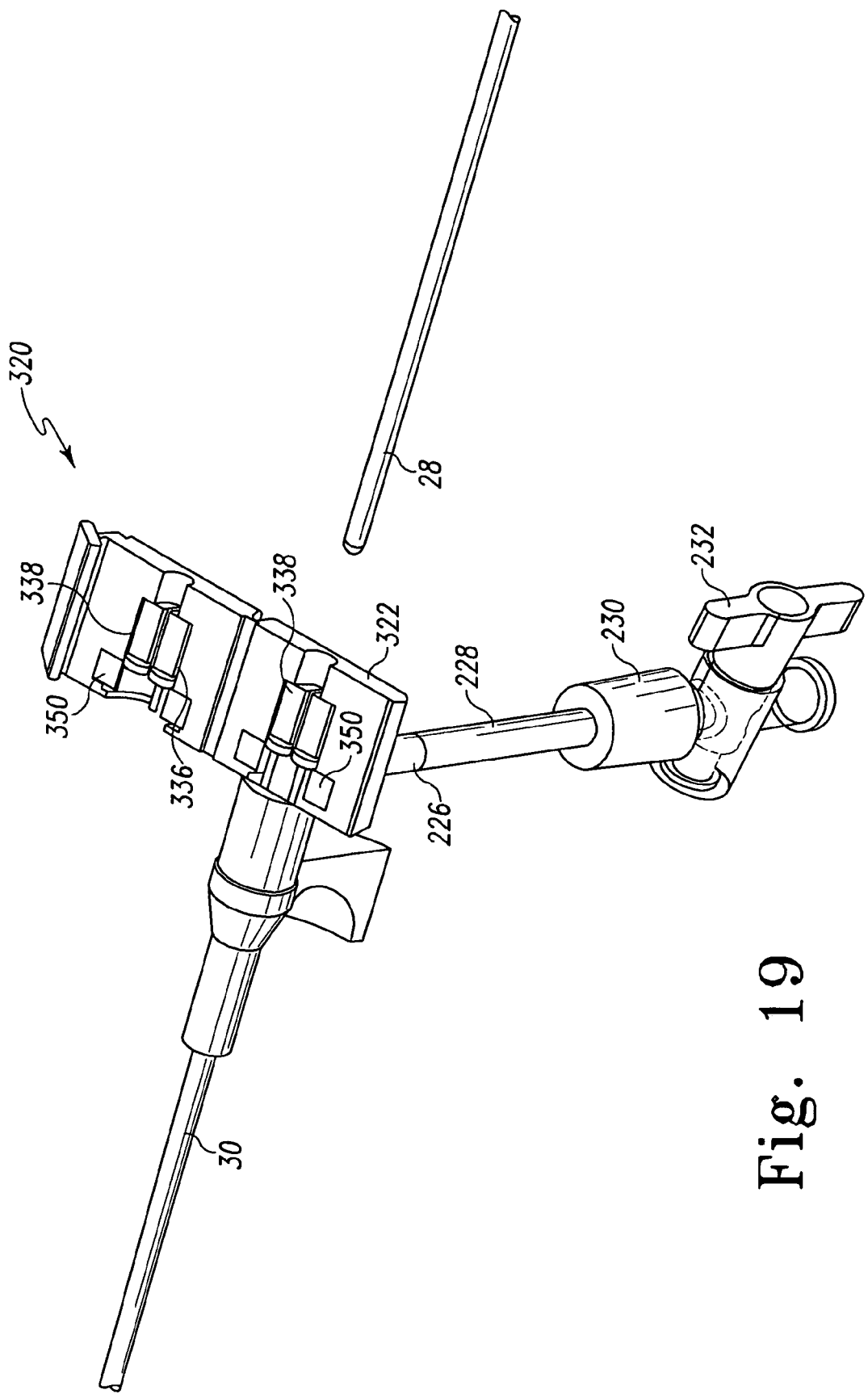
FIG. 19 depicts a perspective view of FIG. 17 with the first medical device disengaged.
Figure 20:
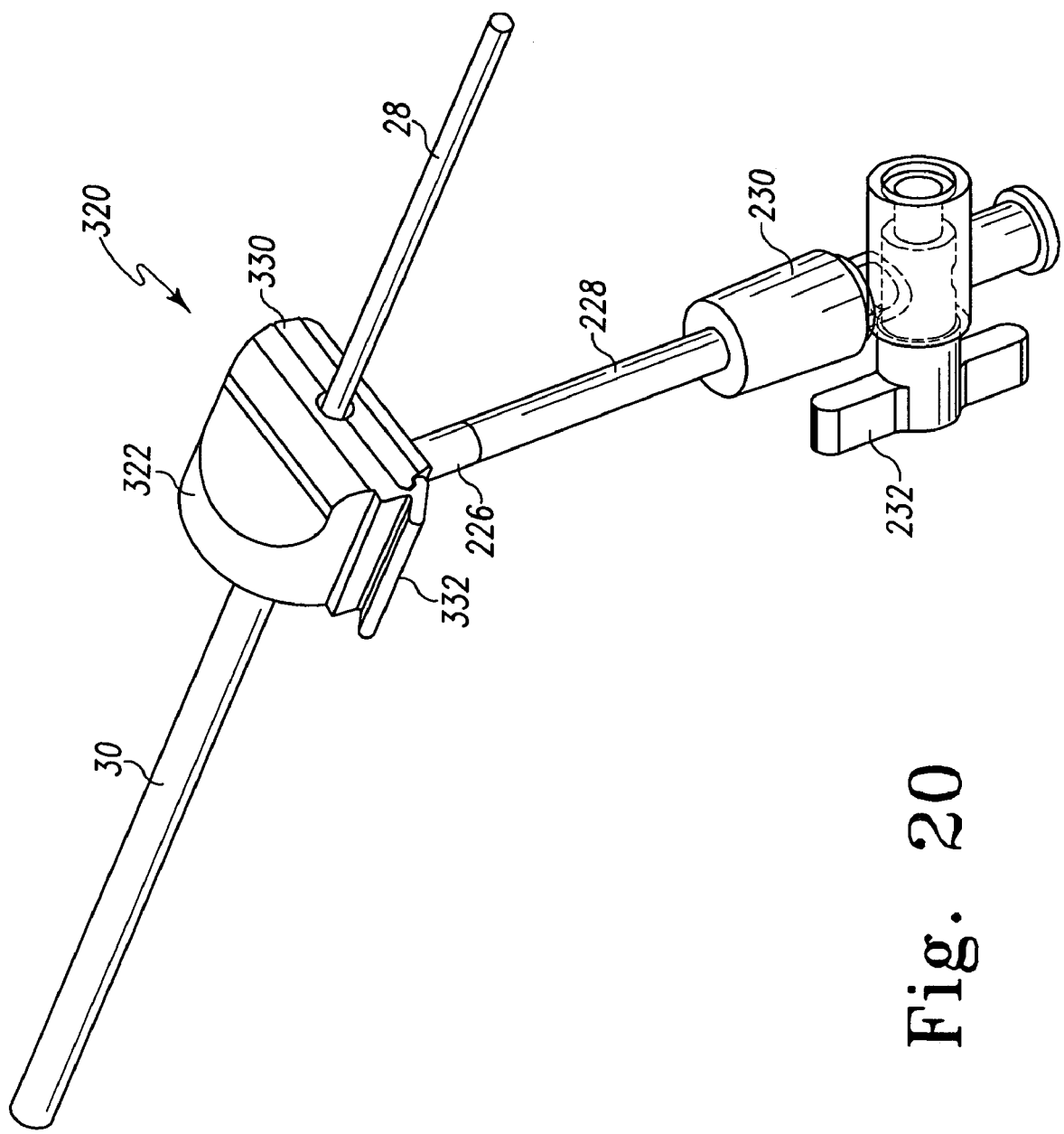
FIG. 20 depicts a perspective view of FIG. 16 of a closed modular hemostatic valve.
Figure 21:
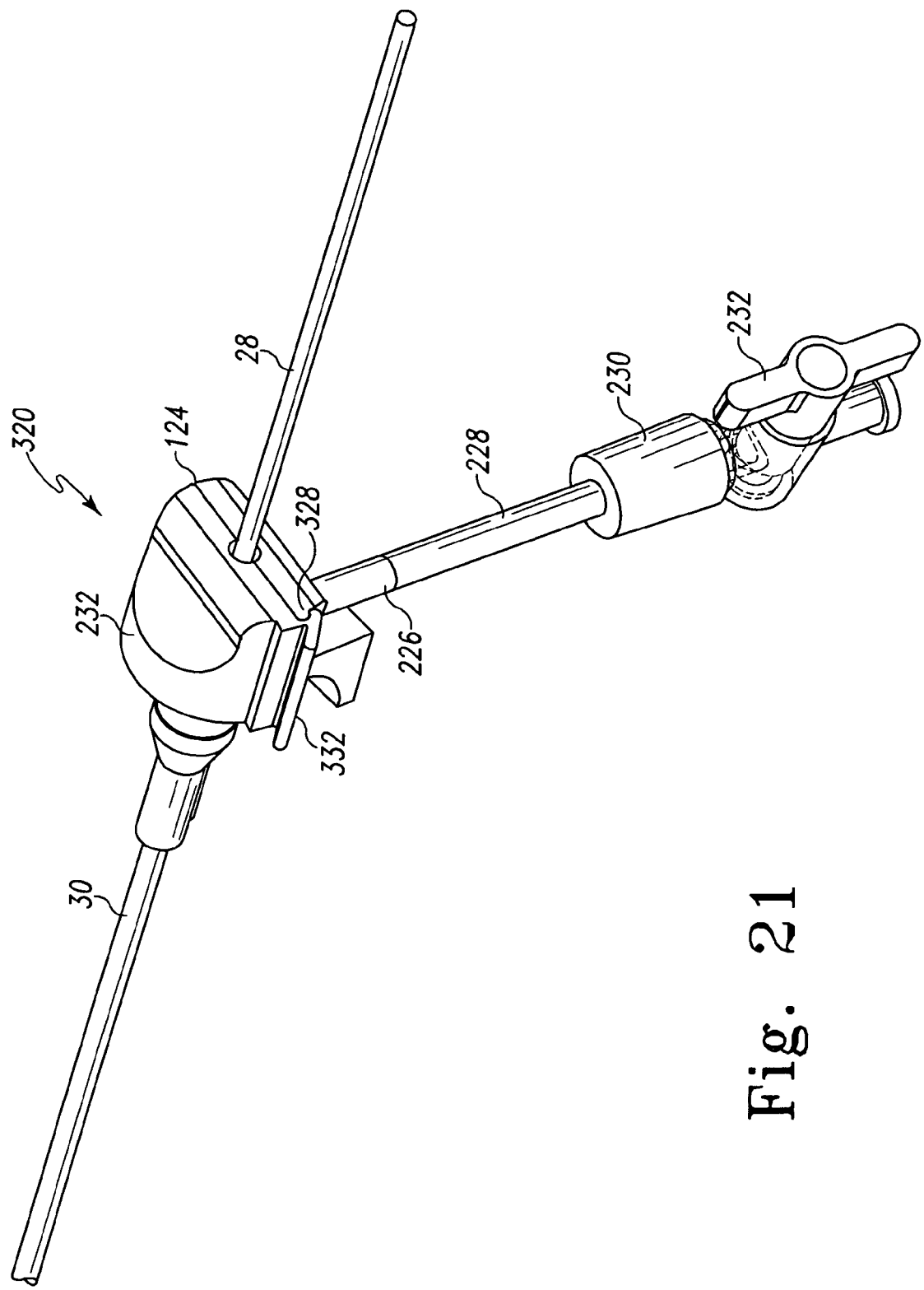
FIG. 21 depicts a perspective view of FIG. 17 of a closed modular hemostatic valve.

In the fourth embodiment, as depicted in FIGS. 16-21, the modular hemostatic valve assembly 320 includes a splittable valve body 322 with a passageway 324. The passageway 324 is designed to permit the passage of the first medical device 28, but substantially preventing or eliminating the leakage or 'flashback' of blood or other bodily fluids. The hemostatic valve assembly 320 is designed for use with the second medical device 30, as depicted in FIGS. 17, 19 and 21.

Figure 10:
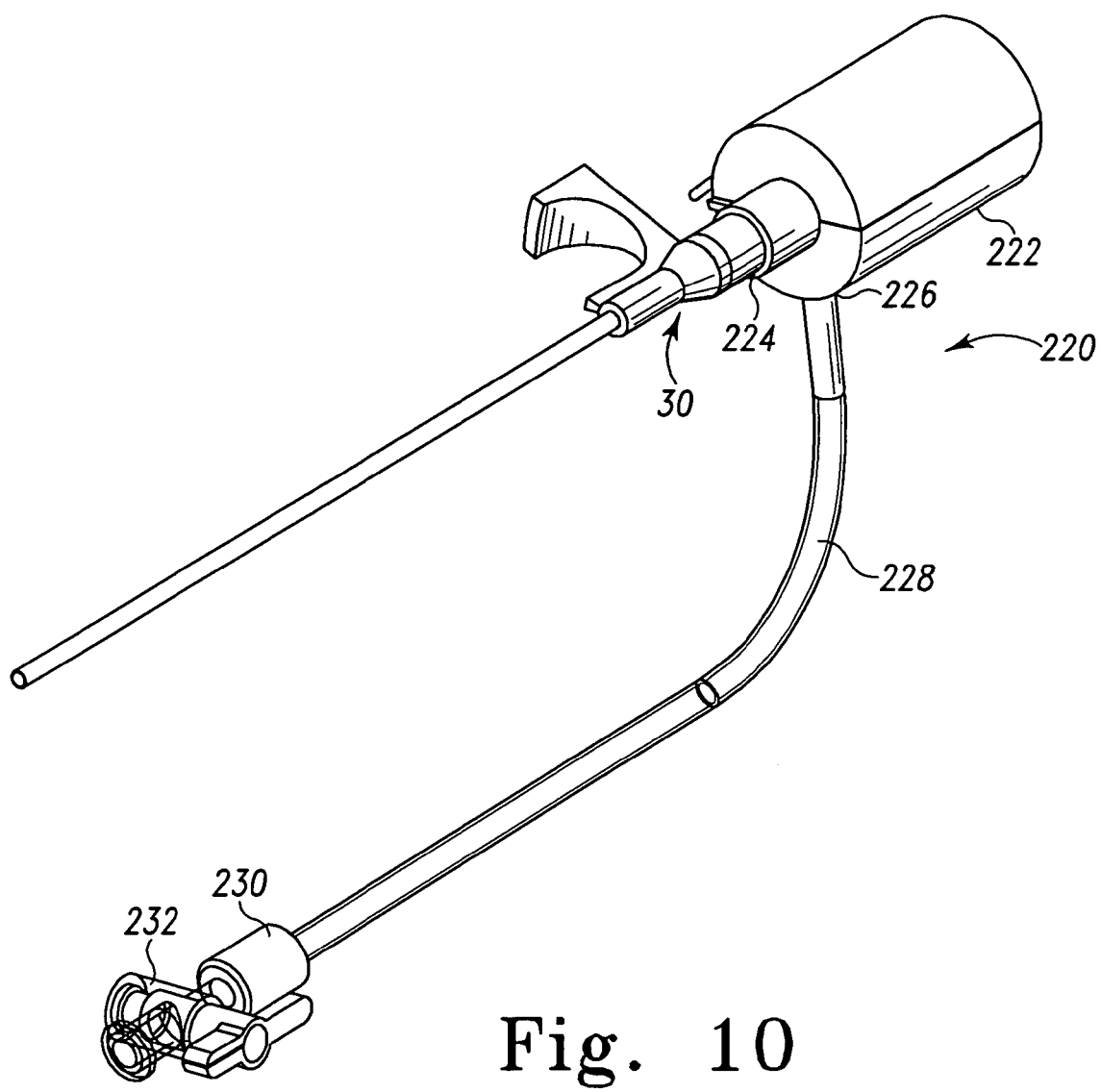
FIG. 10 depicts a perspective view of a modular hemostatic valve including a side port connected to a length of tubing leading to a stop cock valve.

The splittable valve body 322 includes a side port 326 that communicates with the passageway 324, similar to that shown in FIG. 10. The splittable valve body 322 also includes an elongated protrusion 328 on the bottom half 330 of the splittable valve body 322 that is designed to be captured by a coupling hub 332 located at the top half 334 of the splittable valve body 322, similar to that shown in FIGS. 3 and 4. When the elongated protrusion 328 couples with the coupling hub 332, the bottom half 330 and the top half 334 come in contact and close the splittable valve body 322, which also serve to enclose the first medical device 28, as depicted in FIGS. 20 and 21.

The splittable valve body 322 in this embodiment further includes a first engaging member 336 and a second engaging member 338 on each of the bottom half 330 and top half 334 along the passageway 324. The first engaging member 336 has a first protrusion 342 and the second engaging member 338 has a second protrusion 348. In the preferred embodiment, the first 342 and second protrusions 348 are circular in shape. The first engaging member 336 and the second engaging member 338 permit the first medical device 28 to pass therebetween.

Moreover, the bottom half 330 and the top half 334 each includes a clip 350 along the passageway 324, as depicted in FIGS. 17 and 19. In the preferred embodiment, the clip 350 is half-circular in shape. The clip 350 is also configured to capture the first medical device 28. The elements of modular hemostatic valve assembly 320 not specifically discussed here have the same features and functions as the corresponding elements identified by corresponding reference numerals in the previously discussed embodiments.

In the fifth embodiment, the modular hemostatic valve 420 includes an axial telescoping assembly of a stopper 422, a sealing element 24, a body shell 426 and a plug 428, as depicted in FIGS. 7 and 8. The stopper 422 can be an elongated cylindrical member with a passageway 430. In the preferred embodiment, the stopper 422 may include a sealing lip or ring 438 at the stopper distal end 432. The sealing element 24 can be an elongated cylindrical member with a passageway 434. The passageway 434 is in fluid communication with the stopper passageway 430.

The body shell 426 can be a cylindrical shell with a body shell passageway 424. The body shell 426 can be made of silicone or another elastic material. The body shell passageway 424 has a cross shape, although other shapes may be used. The distal end 436 of the body shell 426 can house the sealing element 24 and the stopper 422 axially, with the stopper 422 being placed closer to the shell distal end 436. The stopper ring 438 prevents the stopper 422 from sliding further into the body shell 426, thus maintain the structural integrity of the modular hemostatic valve 420. The body shell passageway 424 is in fluid communication with the sealing element passageway 434 and the stopper passageway 430 to allow the first medical device 28 to pass through. The body shell 426 can also contain a longitudinal adjustment feature 440 on the body shell 426 near the proximal end 442.

The plug 428 can contain a disc-shaped end 444 with a slit 446 at the center, which serves as a passageway 448. This plug passageway 448 is also in fluid communication with the rest of the passageways 424, 430 and 434. The plug 428 can also contain four legs 450 with the narrow ends point away from the disc-shaped end 444. All the legs 450 are configured to be inserted into the cross-shaped passageway 448 at proximal end 442 of the body shell 426. Moreover, a small rectangular block 452 protrudes outward from one of the narrow end of the legs 450. The block 452 is configured to slide into and lock onto the longitudinal adjustment feature 440 of the body shell 426. It is designed to permit the plug 428 to squeeze the sealing element 24 onto a medical device being passed through the modular hemostatic valve 420.

Figure 22:
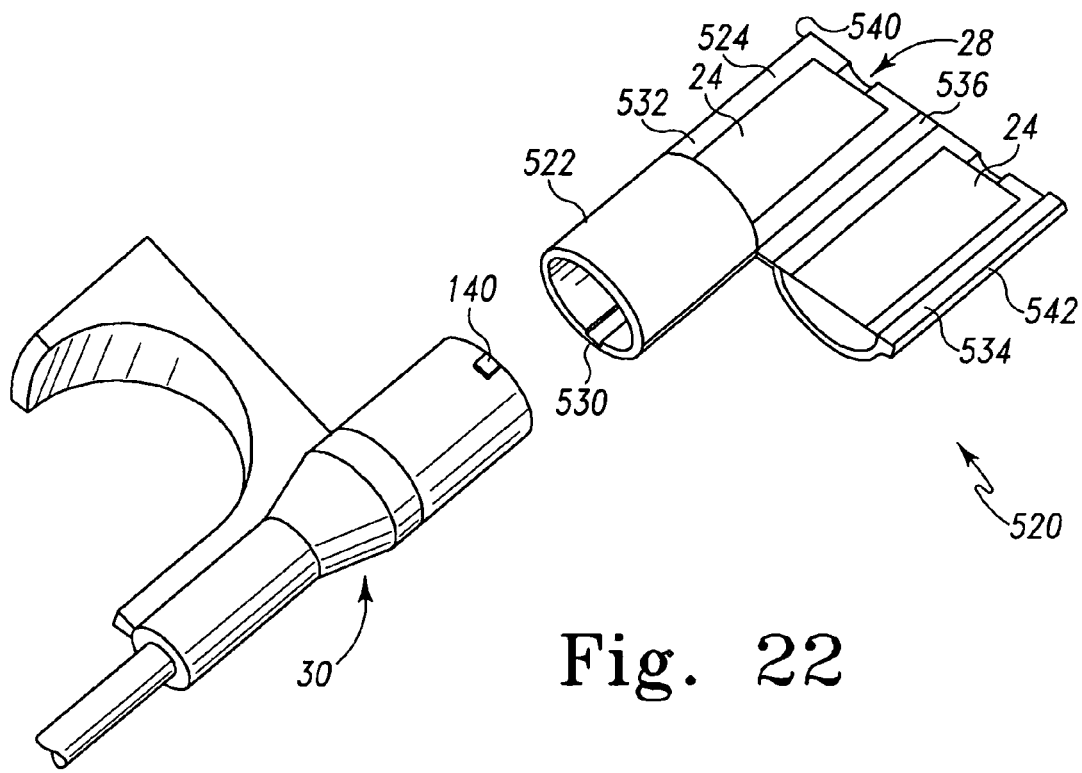
FIG. 22 depicts a perspective view of another modular hemostatic valve having a coupling portion and sealing element receiving portion including a longitudinal living hinge.
Figure 23:
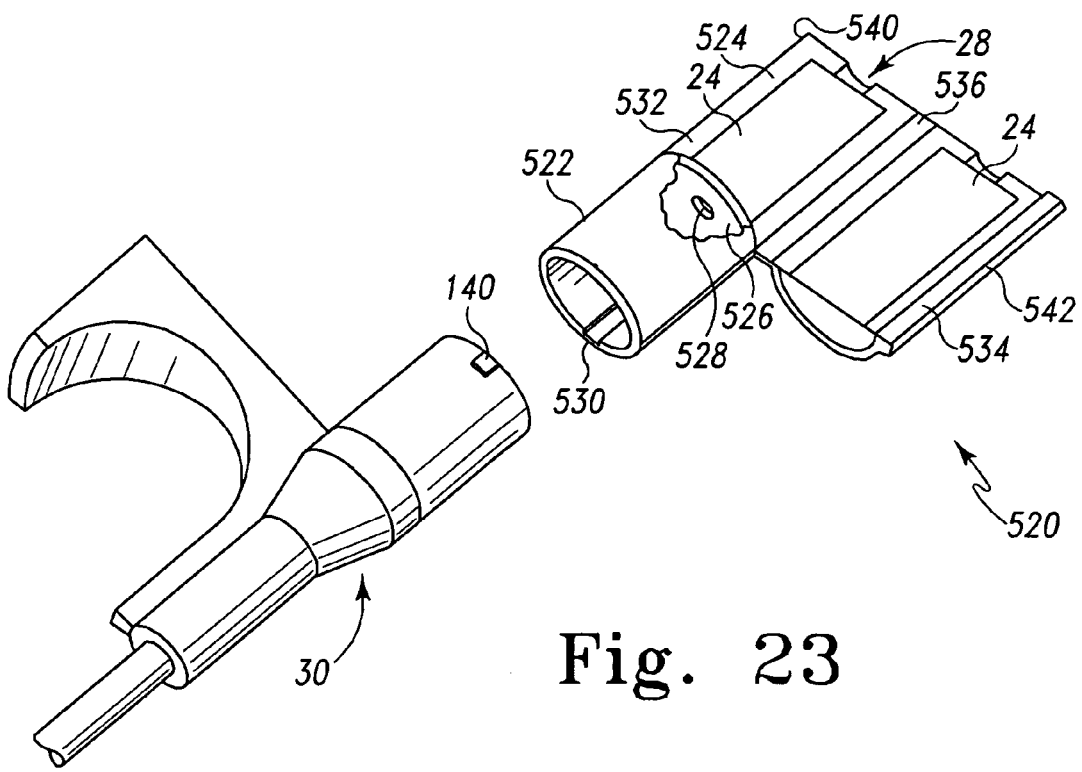
FIG. 23 depicts the perspective view of FIG. 22 partially broken away to reveal the partition and opening between the coupling portion and the sealing element receiving portion.

Yet other embodiments of a modular hemostatic valve assembly 520 of the present invention are depicted in FIGS. 22-26 to include a splittable, generally cylindrical, valve body 522 with a sealing element receiving portion 524. A partition 526 is located between the generally cylindrical, valve body 522 with a sealing element receiving portion 524 as shown in FIG. 23. An opening 528 is in the partition 526 defines a passageway 28, similar to that shown in FIGS. 3 and 4. The passageway 28 is designed to permit the passage of a first medical device (not shown), such as a catheter, dilator, pacemaker lead, etc., but substantially prevent or eliminate the leakage or 'flashback' of blood or other bodily fluids. The hemostatic valve assembly 520 is designed for use with a second medical device 30, shown to be a tubular medical conduit, such as a splittable introducer sheath, as depicted in FIGS. 3, 6, and 8. The generally cylindrical, valve body 522 can include a guide track 530 or other similar feature designed to cooperatively engage any locking protrusion 140 that may exist on the medical device 30.

Figure 24:
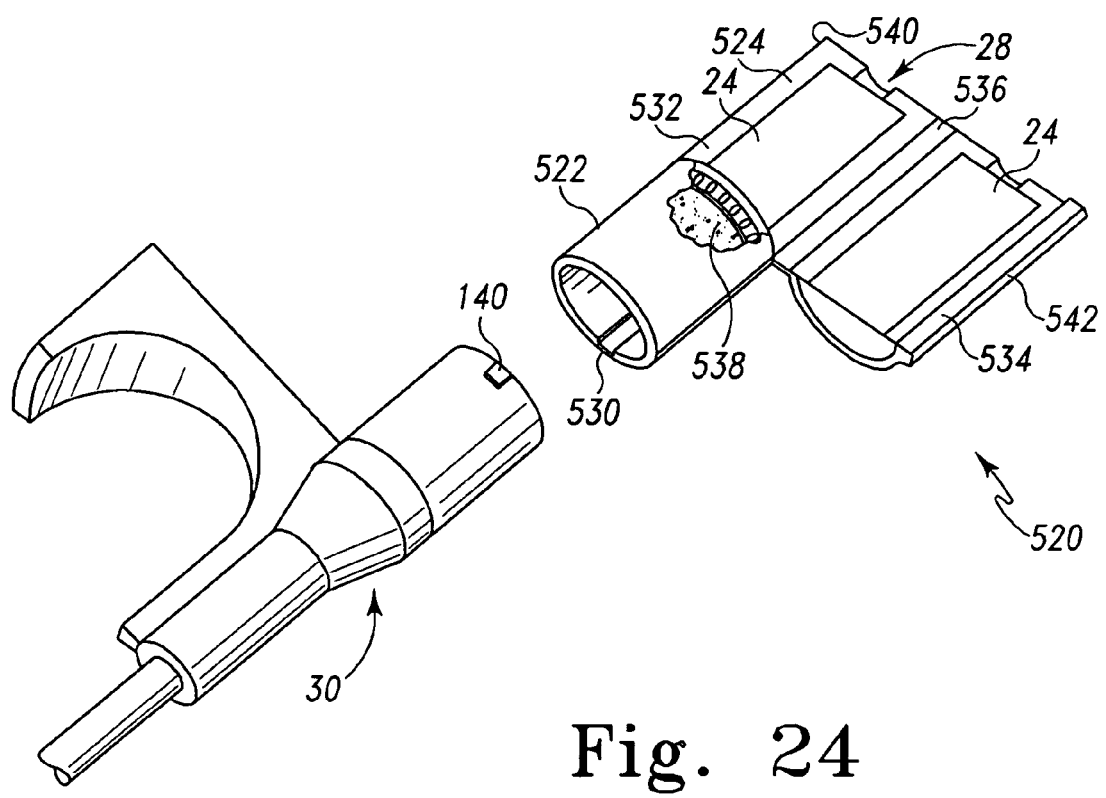
FIG. 24 depicts the perspective view of FIG. 23 with an added foam seal insert in the coupling portion.
Figure 25:
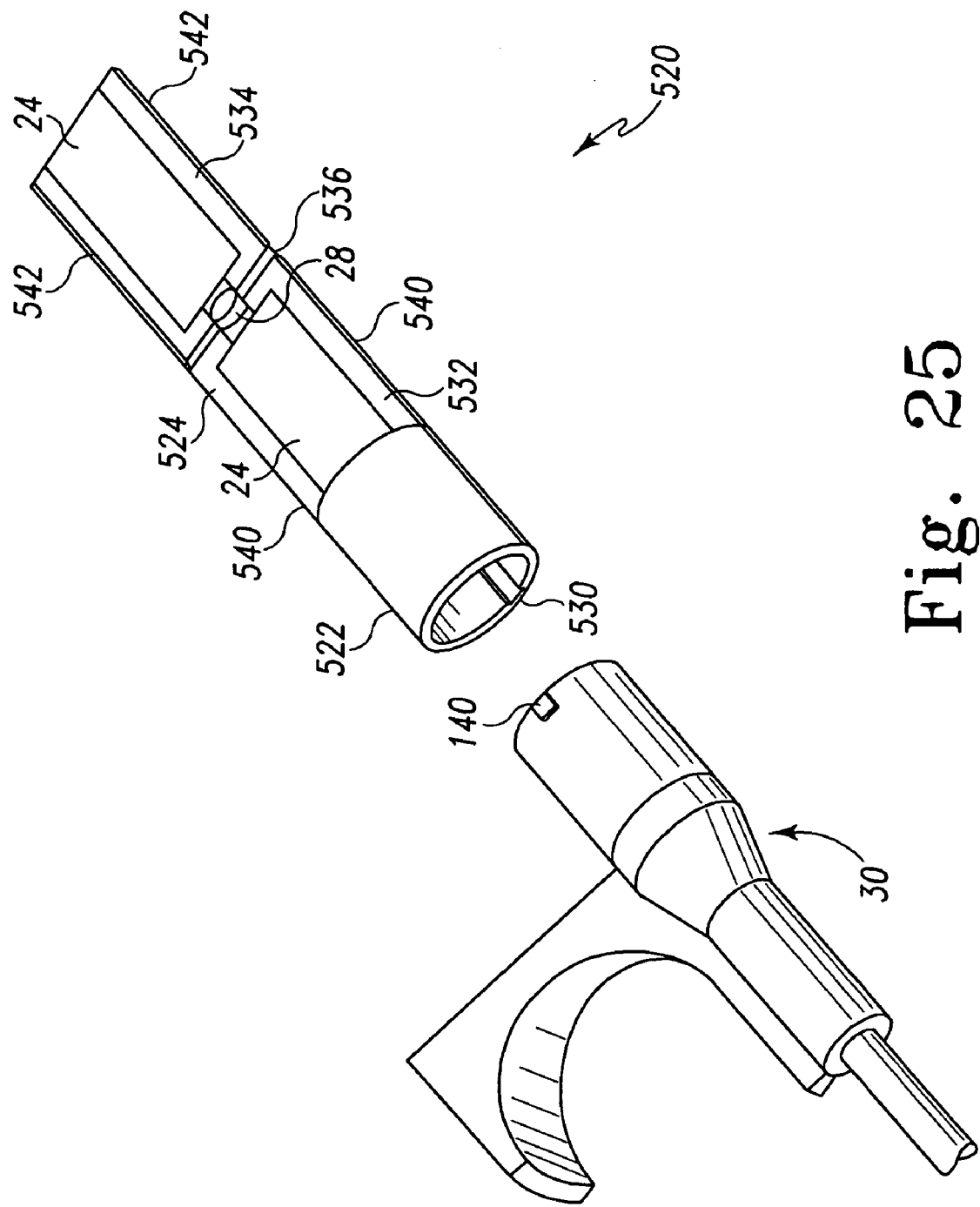
FIG. 25 depicts a perspective view of another modular hemostatic valve having a coupling portion and sealing element receiving portion including a lateral living hinge.
Figure 26:
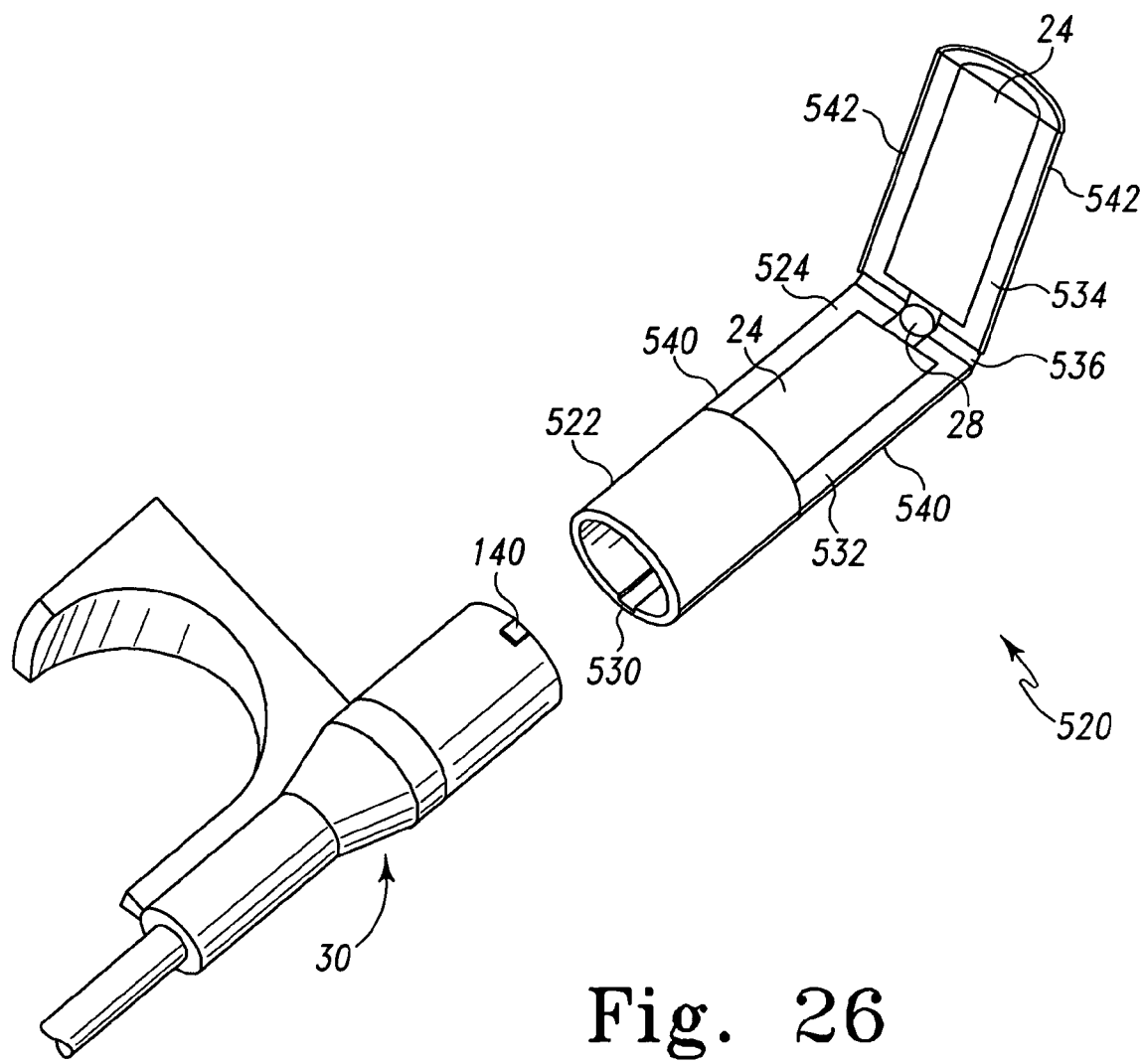
FIG. 26 depicts a perspective view similar to FIG. 25 with the sealing element receiving portion in a partially closed position.

The sealing element receiving portion 524 of the hemostatic valve assembly 520 includes at least two portions 532 and 534 coupled to each other by a living hinge 536. It will be appreciated that the sealing element receiving portion 524 can be configured to include even more than two portions as generally taught by the embodiment shown in FIG. 15. The living hinge 536 can be longitudinally disposed as depicted, for example, in FIGS. 22-24, or laterally disposed as depicted, for example in FIGS. 25 and 26. One of the portions 532 and 534 can also include an elongated protrusion 540, while the other portion can include a coupling hub 542 for capturing the elongated protrusion 540. While the moving portion 534 is shown in FIGS. 22-24 to be coupled to the stationary portion 532 by the living hinge 536 on one side, it will be appreciated that the living hinge 536 and moving portion 534 could be located on the opposite side of the stationary portion 532. Further, while the moving portion 534 is shown in FIGS. 25 and 26 to be coupled to the stationary portion 532 by the living hinge 536, it will be appreciated that the living hinge 536 and moving portion 534 could be coupled to the cylindrical valve body 522.

The sealing element receiving portion 524 of the hemostatic valve assembly 520 can receive any of the sealing elements 24 previously described. Additionally, an additional disk-shaped seal 538 can be included within the generally cylindrical valve body 522 as shown in FIG. 24. The disk-shaped seal 538 can be made of silicone foam that is separately formed from the valve body 522. The seal 538 can be inserted into the body 522 and affixed with silicone adhesive or otherwise secured in placed. The disk-shaped seal 538 can include a small aperture aligned with opening 528 in the partition 526 that facilitates smooth passage of a medical device therethrough. A transverse fissure can be included part way through the seal 538 to allow the seal to split in half along with the remainder of the hemostatic valve 520.

A method of using the modular hemostatic valve of the present invention includes engaging the first medical device 28 with the modular hemostatic valve 20 and engaging the second medical device 30 with the modular hemostatic valve 20. A method of disposing the modular hemostatic valve 20 includes disengaging the first medical device 28 from the modular hemostatic valve 20, disengaging the second medical device 30 from the modular hemostatic valve 20, and splitting open the splittable valve body 20. The method of using and disposing the modular hemostatic valves 120, 220, 320, and 520 can be similarly conducted.

It is thus seen that the present invention has utility in a variety of medical procedures, and that variations and modifications of the modular hemostatic valve assembly of the present invention additional to the embodiments described herein are within the spirit of the invention and the scope of the claims.

We claim:
1. A modular hemostatic valve, comprising:
a splittable valve body, the splittable body defining a passageway; and
a sealing element positioned in the passageway,
wherein the sealing element is configured to facilitate the passage of a first medical device, and the splittable valve body has a first end and a second end,
a first splittable end lead capturing the first end of the splittable valve body, and a second splittable end lead capturing the second end of the splittable valve body, the first and second splittable end leads being spaced from each other and configured to retain the splittable valve body and sealing element as an assembled array,
the splittable valve body including longitudinal guide tracks allowing only axial assembly of the splittable end leads to the splittable valve body.
2. The modular hemostatic valve of claim 1, wherein at least one of the splittable end leads further defines an interfacing region configured to engage a second medical device.
3. The modular hemostatic valve of claim 1, wherein the splittable valve body comprises a first shell and a second shell connected to the first shell to form the passageway.
4. The modular hemostatic valve of claim 1, wherein each of the splittable end leads further comprises an elongated protrusion for engagement with one of the longitudinal guide tracks.
5. The modular hemostatic valve of claim 1, wherein each splittable end capturing an end of the splittable valve body comprises a first half member and a second half member connected to the first half member.
6. The modular hemostatic valve of claim 5, wherein the first and second half members of the splittable end lead define a receiving chamber configured to capture an end of the splittable valve body.
7. The modular hemostatic valve of claim 2, wherein the at least one splittable end lead further comprises a coupling component configured to facilitate the passage of the first medical device and a barbed lead configured to be captured by the second medical device.
8. The modular hemostatic valve of claim 1, wherein the sealing element defines a slot configured to facilitate the passage of the first medical device.
9. The modular hemostatic valve of claim 1, wherein the sealing element comprises of a material selected from a group consisting of silicone foam, viscous liquid glycerin, gel, sponge, densely packed minute beads and stripes of collagen.
10. The modular hemostatic valve of claim 1, wherein the sealing element comprises of a shape selected from a group consisting of a longitudinally extending tube-shaped, a pill-shaped, a plug-shaped with seal rings or seam, and a solid tube with internal ripples.
11. A modular hemostatic valve comprising:
a shell having a distal end and a proximal end,
a passageway extending longitudinally through the shell between the proximal and distal ends;
a longitudinally extending sealing element positioned within the passageway, the sealing element having an internal surface adapted to contact any medical device passing through the shell sufficiently to provide a barrier against fluid backflow though the shell,
the shell including a longitudinal hinge and a mating protrusion and hub permitting quick lateral disassembly from the medical device passing through the shell,
the shell further including a cylindrical interfacing region extending longitudinally from one end of the shell to surround and capture an end of a second medical device, the cylindrical interfacing region including a longitudinal guide track permitting only axial coupling of the second medical device to the cylindrical interfacing region.

12. The modular hemostatic valve of claim 11 wherein the sealing element has an end extending into the cylindrical interfacing region of the shell.

13. The modular hemostatic valve of claim 11, wherein the sealing element comprises of a primary sealing member and a secondary sealing member separated from the primary sealing member by an intermediate wall.

14. The modular hemostatic valve of claim 13, wherein the secondary sealing member further comprises a lateral groove leading to a side port.

15. The modular hemostatic valve of claim 11, further comprising a side port in fluid communication with the passageway, the side port being configured to engage a third medical device.

* * * * *

UNITED STATES PATENT AND TRADEMARK OFFICE
CERTIFICATE OF CORRECTION

PATENT NO. : 7,582,070 B2 Page 1 of 1
APPLICATION NO. : 11/100811
DATED : September 1, 2009
INVENTOR(S) : Goode et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1020 days.

Signed and Sealed this

Fourteenth Day of September, 2010

David J. Kappos
*Director of the United States Patent and Trademark Office*